US012639309B2

(12) United States Patent
Kane

(10) Patent No.: US 12,639,309 B2
(45) Date of Patent: May 26, 2026

(54) ENHANCING RETRIEVAL AUGMENTED GENERATION ACCURACY

(71) Applicant: Telperian, Inc., Austin, TX (US)

(72) Inventor: Michael J. Kane, Austin, TX (US)

(73) Assignee: Telperian, Inc., Austin, TX (US)

( * ) Notice: Subject to any disclaimer, the term of this patent is extended or adjusted under 35 U.S.C. 154(b) by 0 days.

(21) Appl. No.: 19/084,069

(22) Filed: Mar. 19, 2025

(65) Prior Publication Data

US 2025/0298798 A1      Sep. 25, 2025

Related U.S. Application Data

(60) Provisional application No. 63/567,392, filed on Mar. 19, 2024.

(51) Int. Cl.
| | |
|---|---|
| *G06F 17/30* | (2006.01) |
| *G06F 16/2453* | (2019.01) |
| *G06F 16/3329* | (2025.01) |
| *G06N 20/00* | (2019.01) |
| *G16H 10/20* | (2018.01) |
| *G16H 10/60* | (2018.01) |

(52) U.S. Cl.
CPC .... *G06F 16/24542* (2019.01); *G06F 16/3329* (2019.01); *G06N 20/00* (2019.01); *G16H 10/20* (2018.01); *G16H 10/60* (2018.01)

(58) Field of Classification Search
CPC ........ G06F 16/13; G06F 16/24; G06F 16/156; G06F 3/1297; G06N 3/00; G06N 5/00; G05B 13/00; H03M 7/30; H04N 9/8042; G06T 9/00
See application file for complete search history.

(56) References Cited

U.S. PATENT DOCUMENTS

| | | |
|---|---|---|
| 11,586,826 B2 | 2/2023 | Kehler |
| 11,727,243 B2 | 8/2023 | Zhang et al. |
| 11,861,320 B1 | 1/2024 | Gajek et al. |
| 2023/0386520 A1 | 11/2023 | Patterson et al. |
| 2024/0005910 A1 | 1/2024 | Tomkins et al. |

(Continued)

FOREIGN PATENT DOCUMENTS

| | | |
|---|---|---|
| WO | 2024155959 A1 | 7/2024 |
| WO | 2024182041 A1 | 9/2024 |

*Primary Examiner* — Hung D Le
(74) *Attorney, Agent, or Firm* — Pillsbury Winthrop Shaw Pittman, LLP

(57) ABSTRACT

Provided is a method including obtaining a prompt, determining a prompt embedding vector representing the prompt in an embedding space, modifying the prompt embedding vector using a trained model configured to adjust prompt embedding vectors to decrease proximity to vectors of blocks in a data set from which data is retrieved to augment generation by the generative AI model, determining that the modified prompt embedding vector is within a threshold distance to vectors in the embedding space corresponding to one or more blocks in the data set, selecting the one or more blocks in the data set, generating a response using the generative AI model based on the selected one or more blocks in the data set, quantifying an amount of influence of the respective block on corresponding text in the generated response, and providing the response and a representation of the quantified amount of influence as an output.

40 Claims, 3 Drawing Sheets

(56)                    References Cited

U.S. PATENT DOCUMENTS

| | | |
|---|---|---|
| 2024/0265041 A1 | 8/2024 | Rennie et al. |
| 2024/0320310 A1* | 9/2024 | Callegari ................ G06T 11/00 |
| 2024/0386015 A1 | 11/2024 | Crabtree et al. |
| 2024/0428017 A1 | 12/2024 | Shoham et al. |
| 2025/0111169 A1* | 4/2025 | Srinivasan ............... G06N 3/08 |
| 2025/0123814 A1* | 4/2025 | Mcmorran ............ G06N 3/044 |
| 2025/0285720 A1* | 9/2025 | Wellhöfer .............. G16H 10/60 |
| 2025/0321992 A1* | 10/2025 | Madisetti ........... G06F 16/3329 |

* cited by examiner

200

ENHANCING RETRIEVAL AUGMENTED GENERATION ACCURACY

CROSS-REFERENCE TO RELATED APPLICATIONS

This patent claims the benefit of U.S. Provisional Patent Application 63/567,392, filed 19 Mar. 2024, titled ENHANCING RETRIEVAL AUGMENTED GENERATION ACCURACY. The entire content of each afore-listed earlier-filed application is hereby incorporated by reference for all purposes.

BACKGROUND

1. Field

The present disclosure relates generally to computer systems for managing data used in artificial intelligence models and, more specifically, to enhancing retrieval augmented generation accuracy.

2. Description of the Related Art

Retrieval-augmented generation (RAG) systems combine a retrieval mechanism with a generative AI model to improve response accuracy and contextual relevance. The retrieval system searches a data set, such as a database or document corpus, to identify information relevant to a given query. This system may employ various search algorithms to efficiently locate passages or documents that match the input. The retrieved information serves as an external knowledge source that supplements the generative model's output. The generation component, which may be based on large language models, such as GPT (General Purpose Transformer) or BERT (Bidirectional Encoder Representations from Transformers), processes the input query along with the retrieved data to generate a coherent and contextually appropriate response. In some cases, the generation system integrates the retrieved information with its pretrained knowledge, synthesizing a response that reflects both sources.

EXAMPLE EMBODIMENTS

The following is a non-exhaustive listing of some embodiments of the present techniques. These and other embodiments are described in the following disclosure.

Some embodiments may enhance RAG accuracy by refining query alignment, improving response provenance, and increasing response fidelity. Some embodiments may modify query embeddings to increase the likelihood that retrieved data blocks are semantically relevant to the input query. Some embodiments may determine whether the query is directly addressable by the corpus, whether it could benefit from refinement, or whether no relevant data exists in the corpus. Additionally, some embodiments may quantify the influence of each retrieved block on the generated response, which may support the response remaining reflective of the retrieved data. Some embodiments may further attribute portions of a generated response to specific retrieved blocks, increasing transparency and trustworthiness. By incorporating these or other improvements, some embodiments may enhance the reliability and accuracy of RAG-based AI models without necessarily requiring extensive retraining of the underlying large language models. That said, embodiments are not limited to systems that address all or any of the above-listed problems in the art, and not all embodiments have all of the afore-mentioned independently useful features, which is not to imply that any other feature is limiting.

Some aspects include a tangible, non-transitory, machine-readable medium storing instructions that when executed by a data processing apparatus cause the data processing apparatus to perform operations including the above-mentioned process.

Some aspects include a system, including: one or more processors; and memory storing instructions that when executed by the processors cause the processors to effectuate operations of the above-mentioned process.

BRIEF DESCRIPTION OF THE DRAWINGS

The above-mentioned aspects and other aspects of the present techniques will be better understood when the present application is read in view of the following figures in which like numbers indicate similar or identical elements.

Figure 1:
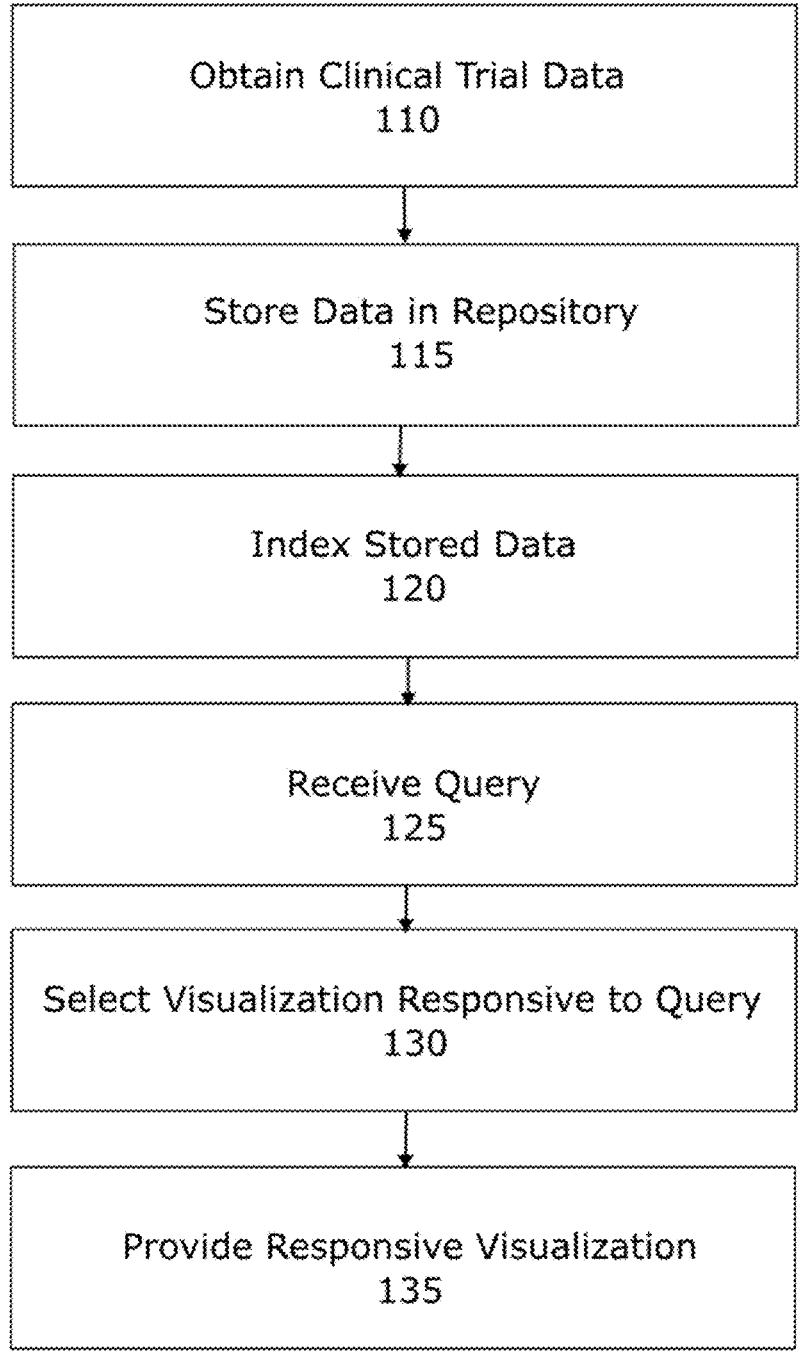
FIG. 1 illustrates a block diagram outlining the steps of an exemplary method for enhancing retrieval augmented generation accuracy.

While the present techniques are susceptible to various modifications and alternative forms, specific embodiments thereof are shown by way of example in the drawings and will herein be described in detail. The drawings may not be to scale. It should be understood, however, that the drawings and detailed description thereto are not intended to limit the present techniques to the particular form disclosed, but to the contrary, the intention is to cover all modifications, equivalents, and alternatives falling within the spirit and scope of the present techniques as defined by the appended claims.

DETAILED DESCRIPTION OF CERTAIN EMBODIMENTS

To mitigate the problems described herein, the inventors had to both invent solutions and, in some cases just as importantly, recognize problems overlooked (or not yet foreseen) by others in the field of retrieval augmented response generation. Indeed, the inventors wish to emphasize the difficulty of recognizing those problems that are nascent and will become much more apparent in the future should trends in industry continue as the inventors expect. Further, because multiple problems are addressed, it should be understood that some embodiments are problem-specific, and not all embodiments address every problem with traditional systems described herein or provide every benefit described herein. That said, improvements that solve various permutations of these problems are described below.

The disclosed technology may be implemented in a variety of domains beyond those explicitly described herein (which is not to suggest other aspects are limiting). While some embodiments may be applied in medical, legal, regulatory, research, and enterprise knowledge management contexts, other embodiments may address distinct technical challenges in other domains. The following examples illustrate some applications of the disclosed technology but should not be interpreted as limiting its scope to any particular implementation, use case, or industry. Some embodiments may enhance information retrieval and response synthesis by leveraging structured and unstructured data sources, refining prompt embeddings, and quantifying the influence of retrieved content on generated outputs. These capabilities may be particularly beneficial in fields where high accuracy, transparency, and information provenance are required, but other embodiments may use variations of these techniques for different retrieval and generation tasks.

RAG systems often aim to improve AI-generated responses by retrieving and incorporating relevant data from a corpus of data (like a corpus of natural language text documents) or a relational database. However, existing RAG embodiments often suffer from query misalignment, response provenance issues, and response fidelity problems. Specifically, many current systems fail to accurately determine whether a query is well-matched to sections of the corpus, leading to irrelevant or incomplete responses. Additionally, RAG systems frequently lack transparency in attributing responses to specific retrieved data, making it difficult to assess the degree of influence any given source has on the generated output. Furthermore, conventional RAG architectures struggle to support generated responses that remain faithful to the underlying retrieved data rather than being influenced by the generative model's pre-trained knowledge. These issues reduce trust in AI-generated outputs, limiting the effectiveness of RAG systems in critical applications such as research, regulatory compliance, and decision support.

Some embodiments may be implemented in a healthcare AI system, wherein retrieved data for RAG may include medical records, clinical guidelines, research articles, or diagnostic data. In some implementations, the system may generate patient-specific recommendations based on retrieved clinical data, wherein the retrieved blocks may include historical patient records, physician notes, laboratory test results, or imaging reports. Some embodiments may process the retrieved blocks to generate insights relevant to an individual patient's medical history, providing contextually informed recommendations for diagnostic procedures, treatment plans, or specialist referrals. In some embodiments, the system may integrate clinical guidelines from medical organizations or regulatory bodies to provide responses that align with best practices and standardized treatment protocols.

In some embodiments, the system may generate summaries of medical literature with ranked provenance scores, wherein the retrieved blocks include peer-reviewed research articles, clinical trial results, or systematic reviews. Some implementations may rank retrieved research findings based on their relevance to a given medical query, wherein generated responses may prioritize the most authoritative and up-to-date sources. In some embodiments, provenance-tracking may be applied to associate specific portions of the response with retrieved literature, providing transparency into the sources that contributed to the generated output. Some implementations may employ ranking mechanisms that account for factors such as study design quality, publication recency, or citation frequency to improve the reliability of retrieved medical literature.

In some embodiments, the system may provide diagnostic support by correlating patient symptoms with retrieved cases from medical literature, electronic health records, or differential diagnosis databases. In some implementations, the system may retrieve clinical cases with symptom presentations similar to those described in the prompt, allowing the generative AI model to identify possible diagnoses based on historical case outcomes. Some embodiments may include disease probability estimation models that weight retrieved cases based on epidemiological prevalence, patient demographics, or risk factors to refine diagnostic suggestions. In some implementations, the system may apply retrieval-guided differential diagnosis methodologies, wherein retrieved cases are dynamically ranked based on their alignment with the patient's reported symptoms, maintaining that generated diagnostic outputs are informed by relevant historical data.

In some embodiments, the system may generate drug interaction analysis based on pharmaceutical data and clinical trial results. In some implementations, the retrieved blocks of data for RAG may include structured databases of known drug interactions, clinical studies on medication efficacy, or real-world evidence reports documenting adverse drug events. Some embodiments may extract relevant findings from retrieved pharmaceutical research to generate patient-specific warnings, recommendations, or dosage adjustments. In some implementations, the system may employ similarity-based retrieval techniques to identify novel drug interactions by comparing retrieved pharmacological data to known interactions, allowing for early detection of potential contraindications.

These and other embodiments may be applied to improve retrieval-augmented AI systems in medical and healthcare settings, maintaining that generated responses reflect relevant clinical data, scientific research, and best practices. Some embodiments may implement additional validation layers, wherein retrieved medical data undergoes secondary verification before being incorporated into a generated response. Some embodiments may involve collaborative retrieval models, wherein multiple data sources, including hospital records, regulatory databases, and research repositories, are queried to produce a comprehensive medical analysis. While these examples describe certain implementations, other embodiments may apply the disclosed technology in different ways to address retrieval-augmented response generation challenges across a variety of domains.

FIG. 1 is a block diagram depicting an exemplary method for improving accuracy of a generated response augmented by data retrieval. The method begins by first obtaining a prompt 110. In some embodiments, the prompt may be a request for a generative AI model (e.g., a transformer among the examples described below) to generate a response (e.g., a natural language text response). The prompt may constitute the entire request for a generated response or may be a portion of a request extracted from a larger input. In some cases, the prompt may be received in a single message, or it may be distributed among multiple messages, or the prompt may be internally generated, e.g., from an upstream generative AI model in a chain of such models. The prompt may take the form of natural language text, structured data, numerical sequences, symbolic representations, programmatic instructions, graph-based input structures, or multimodal data, such as speech, images, or video metadata. In some cases, the prompt may be transformed into an embedding space for processing, e.g., as a single embedding vector, or multiple vectors corresponding to different parts of the prompt or different embedding spaces. In some embodiments, the prompt may be generated automatically, such as by a sequential dialogue system, a system processing machine logs, or an autonomous agent generating contextual queries.

In some embodiments, the prompt received (which includes internal generation of the same) is extrapolated, inferred, or reconstructed from existing data. In some embodiments, a monitoring system processing real-time sensor data may extract anomalies or patterns and use these as implicit prompts to drive AI response generation. Similarly, prompts may be derived from log files, telemetry data, external APIs, metadata annotations, or structured knowledge representations. In some cases, the prompt is received in the form of such a vector or sequence thereof. In some embodiments, the prompt may be transformed before computing its corresponding prompt embedding vector while still being considered a representation of the original prompt. Such modifications may include preprocessing techniques such as removing stop words, normalizing text to a standard form, translating between languages (including from human interpretable languages into machine languages, like intermediate representations between encoders and decoders in autoencoders), correcting spelling errors, replacing text with synonyms, or applying tokenization strategies that segment the prompt into discrete linguistic or semantic units. In some embodiments, the prompt may undergo reformulation wherein the system generates an alternative phrasing of the prompt that preserves its intent while optimizing it for retrieval and generative accuracy. Reformulation may involve paraphrasing, expanding abbreviations, simplifying complex structures, expanding nested phrases, making referents of pronouns explicit, or restructuring the query to improve alignment with the retrieval corpus. In some embodiments, the prompt may be segmented into multiple sub-prompts, wherein each sub-prompt represents a component of the original request that may be processed independently to retrieve contextually relevant information. In some embodiments, the system may generate additional prompts derived from the original prompt, wherein such derived prompts are designed to augment retrieval effectiveness by capturing alternative interpretations, contextual variations, or supplemental queries that enhance information retrieval and response generation. Reference to "a prompt" and then "the prompt" encompasses scenarios where "the prompt" is identical to "a prompt" and where "the prompt" has undergone transformations like those described above applied to "a prompt." In other words, the antecedent may undergo transformation and still qualify as the antecedent to a term following the definite article.

Once the prompt has been obtained, the method may then determine a prompt embedding vector 115 to represent the prompt within an embedding space. The embedding space may be a high-dimensional (e.g., more than 10 dimensions, and typically more than 50, like 256 or more) numerical space in which even higher-dimensional records (like images, natural language text, etc.) are each represented as vectors that capture semantic, structural, or contextual relationships between entities. An embedding vector within this space may be a multi-dimensional numerical representation of an input, typically comprising a fixed or variable-length array of floating-point values. The dimensionality of the embedding space may range from small-scale embeddings such as 32-dimensional representations to high-dimensional latent spaces such as 1024 dimensions or greater, depending on the model architecture and application. Examples include word2vec, GloVe, fastText, BERT embeddings, ELMo, Transformer-based embeddings, TF-IDF, PCA-reduced word vectors, UMAP-reduced embeddings, t-SNE embeddings, doc2vec, autoencoder-based embeddings, Siamese network embeddings, contrastive learning embeddings, latent semantic analysis (LSA), spectral embeddings, node2vec, graph embeddings, sentence-BERT (SBERT), CLIP embeddings, and diffusion model embeddings.

In some embodiments, the embedding space may quantify proximity relationships between objects, wherein closer proximity (in the embedding space) corresponds to a higher degree of similarity based on a criterion (like semantic similarity, sentiment, utility, prognosis, etc). In some embodiments, the proximity within the embedding space corresponds to semantic similarity of the literal text, e.g., the term "king" may be closer to "prince" than the term "car." Some embodiments may associate proximity with topical similarity, wherein the closeness of objects within the embedding space is indicative of a shared topic, sub-topic, or domain-specific thematic grouping. Some embodiments may assign proximity within the embedding space based on functional similarity, wherein proximity indicates entities with similar operational roles, such as functionally equivalent API (application program interface) calls, machine instructions, or chemical compounds with analogous properties. In some embodiments, vectors within the embedding space may be positioned based on graph-based relational similarity, wherein proximity reflects structural relationships such as parent-child relationships in ontologies, citation linkages in research papers, or dependency graphs in computational workflows. In some embodiments, embedding spaces may be arranged to capture chronological progression, where the proximity of objects is determined by their sequential occurrence in a dataset, such as time-series embeddings in predictive analytics models. In some embodiments where embeddings are derived from text, images, audio, or structured metadata, objects in the embedding space may be aligned based on cross-modal feature matching, allowing similarity across different modalities.

In some embodiments, the representation of the prompt in the embedding space may take alternative forms beyond a single vector representation. Instead of a single vector, the representation may be a point or coordinate tuple representing the prompt as a single position in an N-dimensional space without additional transformation metadata. In some embodiments, the representation may be a region or hyperplane where the prompt is not represented as a discrete point but rather as a distribution of possible points, capturing uncertainty or contextual variability. In some embodiments, the representation may be a cluster or set of vectors, allowing the prompt to be represented as a collection of nearby vectors that capture multiple semantic interpretations or variations of the prompt content. In some embodiments, the representation may be a structured graph where nodes correspond to semantic elements of the prompt and edges represent relational dependencies between these elements. In some embodiments, the representation may be a density function over the embedding space, where different areas of the space are assigned probability distributions indicating the likelihood that the prompt corresponds to certain semantic categories or topics.

Some embodiments may then modify the representation of the prompt 120 within the embedding space to decrease proximity to other representations of blocks of a data set corpus from which data is retrieved to augment generation by the generative AI model. In some embodiments, the representation modified may be a prompt embedding vector and it may be modified to decrease proximity to vectors of blocks from the data set corpus, the blocks being represented as vectors in the embedding space.

In some embodiments, the corpus from which data is retrieved may be divided into discrete data blocks through a process referred to as chunking, wherein the corpus is segmented into smaller units to facilitate retrieval and optimize alignment with the modified prompt representation. Chunking may be applied to improve retrieval granularity by maintaining that retrieval operations target contextually relevant portions of the data set rather than entire documents, unstructured text bodies, or large-scale data sources that may contain information unrelated to the prompt. The resulting data blocks may be stored as independent retrieval units within an index or embedding database, allowing for efficient comparison and selection based on proximity to the modified prompt embedding. The chunking methodologies described below may be employed alone or in combination to perform chunking operations. In some embodiments, the system may dynamically select among different chunking strategies based on the characteristics of the corpus, query specificity, or retrieval constraints, maintaining that retrieval-augmented response generation is tailored to the informational structure of the underlying data source. Blocks may be the same size or different size. Blocks may overlap or be non-overlapping. Blocks may be contiguous segments of a record, like a natural language document, such as sentences or paragraphs, or blocks may be non-contiguous parts.

In some embodiments, chunking may be performed based on fixed-length segmentation, wherein the corpus is divided into uniform-sized blocks containing a predefined number of words, characters, tokens, or other units of measurement. In some embodiments, fixed-length segmentation may be implemented to support retrieval efficiency by maintaining a consistent block size across the entire corpus, simplifying indexing and retrieval operations.

In some embodiments, content-aware chunking may be employed to provide that chunk boundaries are determined based on meaningful structural or semantic features rather than arbitrary fixed sizes. In some embodiments, content-aware chunking may involve parsing the corpus based on natural language boundaries, such as sentence delimiters, paragraph structures, or document section headings, maintaining that each block retains complete contextual units. In some embodiments, content-aware chunking may utilize topic modeling algorithms such as Latent Dirichlet Allocation or transformer-based embeddings to segment the corpus into thematically consistent blocks. In some embodiments, content-aware chunking may apply recursive structure-aware segmentation, wherein the corpus is analyzed at multiple hierarchical levels, allowing for adaptation between finer-grained and coarser-grained chunking depending on the retrieval needs of the system.

In some embodiments, adaptive chunking may be performed, wherein chunk sizes and boundaries are dynamically adjusted based on retrieval success rates, document complexity, or query characteristics. In some embodiments, adaptive chunking may use feedback from previous retrieval interactions to modify chunking parameters, maintaining that frequently retrieved data blocks are refined to increase relevance while low-retrieval-value blocks are merged or expanded to improve coverage. In some embodiments, an adaptive chunking system may integrate a reinforcement learning-based approach, wherein chunking strategies are optimized over time by rewarding segmentations that yield higher retrieval fidelity while penalizing segmentations that result in retrieval failure or incomplete context matching.

In some embodiments, overlapping chunking may be applied, wherein individual chunks contain portions of adjacent text or data blocks to preserve contextual continuity. Overlapping chunking may involve configuring a predefined overlap percentage between consecutive chunks, maintaining that no relevant information is lost due to arbitrary segmentation boundaries. In some embodiments, overlapping chunking may be applied when processing documents with long-range dependencies, such as legal contracts, medical case reports, or regulatory filings, where continuity between sequential sections is necessary to maintain contextual coherence.

In some embodiments, hierarchical chunking may be implemented, wherein multiple levels of chunking are applied to create nested representations of data blocks at different granularities. Hierarchical chunking may involve generating fine-grained chunks that capture small semantic units, such as individual sentences, while simultaneously maintaining coarse-grained chunks representing entire paragraphs or document sections. In some embodiments, hierarchical chunking may facilitate multi-resolution retrieval strategies, allowing the system to first retrieve high-level conceptual blocks before refining the search to more specific sub-chunks if required.

In some embodiments, the data set may be indexed by computing embedding vectors in the embedding space for text blocks using hierarchical navigable small world (HNSW) graphs or content-aware chunking strategies to optimize retrieval efficiency. In some implementations, hierarchical navigable small world graphs may be employed to create an efficient, scalable index for rapid nearest-neighbor searches, wherein text block embeddings are structured within a multi-layered graph that allows for logarithmic-time complexity search operations. HNSW indexing facilitates high-speed approximate nearest neighbor retrieval by leveraging graph traversal techniques that balance search efficiency with retrieval accuracy, maintaining that the modified prompt embedding vector can quickly identify the most relevant blocks in the data set. In some embodiments, the graph structure may be dynamically updated as new data blocks are introduced into the corpus, allowing for continuous adaptation of retrieval pathways.

In some embodiments, content-aware chunking strategies may be integrated with the indexing process to further enhance retrieval precision, wherein text blocks are assigned embeddings based on linguistic coherence, topic segmentation, or structural attributes before being indexed. In some implementations, embeddings may be generated using transformer-based models trained on domain-specific corpora to provide that text blocks with similar semantic meanings are positioned closer within the embedding space. Some embodiments may employ a hybrid approach wherein hierarchical chunking is combined with HNSW indexing, allowing for retrieval at multiple levels of granularity, wherein high-level chunks may first be retrieved based on broad contextual alignment before fine-grained retrieval is conducted within the selected regions. These and other indexing techniques may be used individually or in combination to create an optimized retrieval framework that balances computational efficiency with response fidelity.

In some embodiments, modifying the prompt representation in the embedding space may include providing a reformulated query using a natural language processing model trained based on retrieval accuracy. In such embodiments, a query reformulation model may take as input the original prompt and apply a transformation process to generate a semantically equivalent (or semantically proximal) but structurally refined version of the query that is expected to retrieve more relevant information from the data set corpus. The query reformulation model may be trained using supervised learning, reinforcement learning, or contrastive learning techniques, where positive examples may be derived from prior retrieval interactions that resulted in high-accuracy generations, and negative examples may be derived from retrieval interactions that resulted in inaccurate, incomplete, or irrelevant responses. In some embodiments, the reformulated query may be derived using a sequence-to-sequence language model trained to maximize retrieval fidelity, wherein the training objective may include minimizing the difference between the generated response and a human-verified correct response given the same retrieved data. In some embodiments, the reformulation may introduce synonyms, paraphrased text, or additional context extracted from a domain-specific lexicon or knowledge base to improve retrieval effectiveness. In some embodiments, the reformulated query may undergo multiple iterations of refinement, where the reformulated output itself is evaluated for retrieval effectiveness and iteratively improved using reinforcement learning with feedback from retrieval performance metrics.

In some embodiments, modifying the prompt representation in the embedding space may involve adjusting the scalars of the prompt embedding vector, wherein individual elements of the multi-dimensional representation are altered to shift the positioning of the embedding within the space. This modification may be performed by applying scaling factors to specific dimensions of the embedding, wherein weightings may be adjusted to emphasize or de-emphasize certain features based on relevance to the retrieval task. In some implementations, modifying the scalars may include reweighting components of the embedding vector associated with term importance, wherein terms relevant to retrieval are amplified while less significant terms are down weighted to refine the query's influence on retrieval selection.

In some embodiments, modifying the prompt embedding vector may involve applying a transformation function that alters the geometric properties of the vector, such as rotating the vector within the embedding space to align with a cluster of relevant documents while maintaining semantic consistency. Some embodiments may involve projecting the embedding onto a lower-dimensional manifold optimized for retrieval, wherein the modified representation retains only the most critical retrieval-related features while reducing dimensional redundancy. In some implementations, the modification may include adding or subtracting bias vectors derived from domain-specific embeddings, allowing the prompt embedding to shift toward specialized terminology or structured data representations. Some embodiments may involve non-linear transformations, such as applying a learned neural projection layer that dynamically adjusts the prompt embedding based on corpus-specific retrieval distributions. These and other approaches may be used alone or in combination to modify the prompt representation within the embedding space, facilitating optimal alignment with relevant retrieval results while preserving the semantic integrity of the original query.

In some embodiments, modifying the prompt embedding vector may include adjusting the prompt representation in the embedding space based on a stored session history, wherein the stored session history relates to previous iterations of the described method, their success rates, their accuracy rates, or other performance metrics. In some embodiments, a session history may be maintained as a log of prior prompt-retrieval-response interactions, wherein each entry in the session history contains metadata describing the retrieval effectiveness, such as the similarity scores of retrieved blocks, response fidelity measures, and external user feedback when applicable. The modification of the prompt embedding vector may be performed by analyzing trends in the session history to identify patterns of retrieval failure, misalignment, or suboptimal query structuring and then applying an embedding transformation function that optimizes retrieval accuracy based on the learned patterns.

In some embodiments, the adjustment may involve applying a learned correction vector derived from prior retrieval interactions, wherein the correction vector represents the direction in the embedding space that historically led to higher retrieval fidelity.

In some embodiments, modifying the prompt representation based on session history may involve clustering prior retrievals within the embedding space to detect patterns of successful and unsuccessful retrieval attempts, where the clustering process may be performed using hierarchical clustering, k-means, or density-based spatial clustering (e.g., DB-SCAN). Once clusters of successful retrieval interactions are identified, the modification function may reposition the prompt embedding vector toward the center of the cluster of historically successful retrievals while reducing its proximity to clusters associated with retrieval failures. In some embodiments, a memory-augmented neural network may be employed to store and retrieve session-specific modifications, allowing a generative AI system to apply retrieval-aware transformations dynamically during live interactions based on historical performance.

In some embodiments, the modification of the prompt representation may involve applying a learned projection function that maps the original prompt embedding vector into a transformed subspace within the embedding space that has been optimized for retrieval fidelity. This learned projection function may be trained using contrastive learning techniques, wherein the objective is to maximize the distance between the modified prompt embedding and known irrelevant retrievals while minimizing the distance to known relevant retrievals. In some embodiments, this transformation may be performed using an encoder-decoder architecture wherein the encoder refines the original prompt embedding, and the decoder reconstructs an optimized query embedding that is expected to yield improved retrieval results.

In some embodiments, the modification may be performed using a trained model designed to reduce the proximity of the prompt representation object to one or more of the blocks within the data set. In some embodiments, the trained model may be a supervised learning model that processes labeled datasets, where each training instance consists of an original prompt, an optimized transformed prompt, and corresponding retrieval performance metrics. The model may be trained using a loss function that penalizes modifications that increase proximity between the transformed prompt representation and irrelevant blocks while reinforcing transformations that improve retrieval effectiveness. Training data for such a model may be obtained by analyzing historical retrieval queries, ranking the relevance of retrieved blocks, and applying query transformations that optimize retrieval outcomes.

In some embodiments, the trained model may be a reinforcement learning model that iteratively adjusts the prompt representation based on feedback derived from retrieval quality assessments. The reinforcement learning model may be structured as a Markov Decision Process in which a retrieval system functions as an external feedback mechanism for evaluating prompt embedding transformations. The state space in the reinforcement learning environment may include representations of prompt embedding vectors before modification, while the action space may define numerical transformations applied to the prompt embedding vectors within the embedding space. The model may operate under a reward function that assigns positive rewards when a modified prompt decreases proximity to non-relevant data set blocks while maintaining or increasing proximity to relevant blocks. The training process may involve iteratively modifying prompt embeddings, retrieving blocks from the data set based on similarity to the modified embeddings, and computing a reward signal that reflects the retrieval quality of the selected blocks relative to the original prompt embeddings. The model may adjust transformation strategies by dynamically updating its learned policy, optimizing embedding modifications over time to maximize retrieval fidelity. Training may continue across multiple query-block instances, allowing the system to adapt to different retrieval contexts and improve retrieval accuracy across diverse corpora.

In some embodiments, the trained model may be designed using contrastive learning techniques, wherein prompt modifications are optimized based on distance metrics that differentiate between high-relevance and low-relevance retrievals. A contrastive learning approach may train an encoder network to maximize the distinction between transformed prompts that lead to successful retrieval and those that result in irrelevant or low-confidence retrievals. This process may involve the use of triplet loss or other metric-learning objectives, maintaining that the modified prompt representation is positioned optimally within the embedding space relative to relevant and non-relevant retrieval candidates.

In some embodiments, the trained model may incorporate elements of adversarial training, where a discriminator network is trained to evaluate whether a given prompt transformation leads to a high-quality retrieval. The modification model may iteratively refine prompt representations in an effort to fool the discriminator into classifying transformed prompts as optimal retrieval queries. This approach may be particularly effective in dynamically adjusting prompt modifications across different corpora, facilitating robust performance in retrieval-augmented generative AI applications.

In some embodiments, modifying the prompt embedding vector may involve enforcing retrieval constraints within the embedding space. For example, in security-sensitive applications, certain retrieval pathways may be restricted, requiring the prompt modification function to adjust the embedding vector in a way that supports retrieval remains within predefined boundaries. This may be accomplished through geometric transformations that map the prompt embedding onto a constrained subspace, facilitating compliance with retrieval policies.

In some embodiments, a representation of the modifications applied to the prompt embedding vector may be generated to provide transparency in how the prompt representation is altered before retrieval. The representation of the modifications may be structured as a set of transformation parameters that describe the specific numerical adjustments applied to the embedding vector. In some implementations, these transformation parameters may include the nature of the modification, such as scalar adjustments, vector re-weighting, or projection onto a learned subspace. In some embodiments, the representation may capture the incremental modifications performed in a multi-stage process, wherein each transformation step is logged and recorded as part of the final modification representation. The representation may include intermediate embedding states, allowing for traceability of how the prompt embedding vector evolved through different processing stages.

In some embodiments, the representation of the modifications may be used as input to a generative artificial intelligence model, wherein the model generates a natural language explanation describing the modifications made to the prompt embedding vector. The generative AI model may take as input (e.g., in the context window, at run time, after the model is trained) the transformation parameters, the original prompt representation, and the modified prompt embedding vector, generating a human-readable description that explains how the modifications were applied. In some implementations, the generative AI model may use retrieval-based augmentation to maintain that the explanation includes references to specific transformations, such as distance-based shifts in the embedding space or the application of domain-specific biasing mechanisms. Some embodiments may employ a structured explanation generation approach, wherein the generated description is formatted using a predefined schema that categorizes different types of modifications, such as semantic re-weighting, retrieval alignment, or contextual adaptation.

In some embodiments, the generated explanation may be used for debugging or auditing purposes, allowing users to understand how the modified prompt embedding vector was derived. In some implementations, the explanation may be presented in a user interface alongside visualization tools that depict changes in the embedding space, such as dimensional reduction plots that illustrate the movement of the prompt embedding vector before and after modification. Some embodiments may allow for interactive review, wherein users can query specific aspects of the modification process and receive detailed breakdowns of how individual transformations affected the prompt representation.

In some embodiments, the generated natural language output may be stored in a knowledge base for future reference, allowing for retrospective analysis of prompt modifications and their impact on retrieval performance. In some implementations, the explanation may be used as training data for refining prompt modification models, wherein historical explanations are used to develop more interpretable and context-aware transformation functions. Some embodiments may employ reinforcement learning techniques wherein user feedback on explanation accuracy is used to iteratively improve the quality of the generated descriptions, maintaining that the AI-generated explanations remain aligned with human expectations and retrieval transparency requirements.

As used in this disclosure, the terms "modify" or "modifying" (and the like) should not be construed as being limited to operations performed on a record at single memory address or data instance, as the terms (and the like) encompass both direct in-place modifications and modifications that result in the creation of a new version with the modification stored at a different memory location. In some embodiments, modifying the representation of the prompt within the embedding space may involve updating the numerical values associated with the prompt embedding vector in its original memory address. In other embodiments, modifying the representation may involve generating a new version of the prompt embedding vector with adjusted values and storing this new version at a separate memory address while preserving a reference to its relationship with the original. The choice of whether to modify in-place or generate a new instance may depend on factors such as memory optimization, computational efficiency, or architectural design constraints of the system. Regardless of the specific embodiment, both approaches constitute modification as used in this disclosure, maintaining that the system maintains flexibility in handling memory allocation and data transformations without altering the functional definition of modification within the scope of this invention.

Some embodiments may then select one or more blocks in the data set 125. This selection may be based on a determination that the modified prompt embedding vector is within a threshold distance to vectors representing one or more blocks of the data set in the embedding space. A threshold distance, as used in this disclosure, may define a predefined or dynamically computed measure within the embedding space that determines whether a retrieved block is considered sufficiently relevant to the modified prompt embedding vector. The threshold distance may be defined as a static numerical value, such as a fixed cosine similarity threshold, Euclidean distance threshold, or dot product similarity threshold, wherein blocks whose vector representations fall within this predefined threshold relative to the modified prompt embedding vector are selected. In some embodiments, the threshold distance may be dynamically adjusted based on contextual factors, such as query specificity, historical retrieval accuracy, or corpus structure. In some embodiments, adaptive thresholding may be performed using machine learning models trained to predict the optimal threshold distance based on retrieval effectiveness metrics, wherein prior retrieval attempts are analyzed to determine the relationship between threshold values and retrieval accuracy. In some embodiments, the threshold may be defined using a probabilistic distribution over distances in the embedding space, wherein a confidence interval is applied to determine which blocks are likely to be relevant based on statistical measures such as standard deviation scaling, kernel density estimation, or Bayesian inference models. The threshold may further be refined using reinforcement learning techniques, wherein the system iteratively optimizes the threshold distance based on a reward function that penalizes unnecessary retrieval expansion while maximizing the retrieval of relevant information.

As used in this disclosure, the term "meeting a threshold" or "satisfying a threshold" or the like should not be construed as being limited to a strict equality condition but rather should be understood to encompass a variety of comparative relationships depending on the context in which the threshold is applied, e.g., greater than, greater than or equal to, less than, or less than or equal to. For example, these terms cannot be designed around by merely multiplying a value by negative one and reversing the comparison from greater than to less than. In some embodiments, meeting a threshold may mean that a value is greater than or equal to the threshold, while in other embodiments, meeting a threshold may mean that a value is less than or equal to the threshold. Similarly, in some embodiments, a threshold condition may be satisfied when a value exceeds a specified (e.g., predetermined or dynamically determined) limit, while in other embodiments, a threshold condition may be satisfied when a value falls below a specified limit. Furthermore, the mathematical formulation of a threshold should not be interpreted in a way that allows circumvention through simple transformations, such as multiplying all values by negative one to invert inequality relationships.

In some embodiments, selecting blocks may include federated retrieval across multiple corpora (e.g., internal or external, local or distributed), wherein retrieved blocks are selected not only from a single centralized knowledge base but also from distributed data repositories, external databases, or independently maintained corpora. Federated retrieval may involve sending retrieval queries to multiple independent data sources, each of which may maintain its own indexing, storage, or retrieval mechanisms. In some embodiments, federated retrieval may involve a cross-system embedding alignment process, wherein embeddings from different corpora are projected into a unified embedding space, maintaining that representations from diverse data sources can be meaningfully compared. In some embodiments, retrieval may be performed using a hybrid approach that combines direct retrieval from a local corpus with API-based retrieval from remote or external corpora, wherein external data sources may return candidate blocks ranked based on relevance scores computed in their respective indexing systems. In some embodiments, federated retrieval may utilize a consensus-based ranking system, wherein multiple corpora return independently ranked retrieval results, and the system applies an aggregation function, such as a voting mechanism, weighted ranking fusion, or ensemble-based retrieval selection, to determine the final set of retrieved blocks. In some embodiments, federated retrieval may further involve differential retrieval weightings, wherein different corpora are assigned varying levels of retrieval priority based on domain-specific criteria, trustworthiness, or real-time data recency.

In some embodiments, selection may be performed by retrieving a predefined (or dynamically determined) number of the closest blocks to the modified representation of the prompt in the embedding space, wherein the selection process ranks all blocks in the corpus based on their proximity to the modified prompt embedding vector and retrieves a fixed number of top-ranked blocks. In some embodiments, selection may involve applying a ranking-based retrieval model trained to prioritize blocks based on multiple retrieval signals, wherein embeddings are supplemented with metadata such as block frequency, prior retrieval success rates, or document importance scores to determine retrieval rankings. In some embodiments, selection may be based on a minimum information coverage constraint, wherein blocks are selected to maximize semantic diversity and minimize redundancy, maintaining that selected blocks collectively capture a broad range of relevant concepts rather than retrieving highly similar information.

In some embodiments, methodologies for determining proximity between the modified embedding vector and blocks in the data set may include cosine similarity measurements, Euclidean distance computations, Manhattan distance evaluations, Minkowski distance, or kernelized similarity functions. In some embodiments, retrieval may incorporate graph-based distance calculations, wherein embeddings are connected within a knowledge graph, and proximity is determined based on shortest-path calculations, node centrality measures, or network diffusion processes. In some embodiments, learning-based proximity estimation models may be used to dynamically refine similarity computations, wherein a retrieval scoring function is trained to predict the likelihood that a block is relevant given a modified prompt representation, adjusting retrieval parameters based on real-time data patterns.

In some embodiments, reranking may be performed to reorder the selected blocks based on their proximity to the prompt embedding vector in the embedding space before generating a response. The computer-implemented method may comprise computing, with the computer system, a proximity measure between each selected block and the prompt embedding vector, wherein the proximity measure represents a degree of semantic or contextual similarity between the block and the modified prompt representation.

Some embodiments may rank the selected blocks based on their respective proximity measures, wherein blocks with the highest relevance scores are assigned higher priority for response generation. In some implementations, the reranking process may involve normalizing the proximity scores across the selected blocks to generate a ranking distribution that is independent of absolute vector magnitudes. In some embodiments, additional weighting factors may be applied during reranking, wherein blocks that meet predefined retrieval conditions, such as higher source reliability, recency, or domain specificity, are assigned an adjusted relevance score before finalizing the ranking order.

In some embodiments, reranking may be performed iteratively, wherein the ranking of the selected blocks is refined across multiple evaluation passes before response generation. In some implementations, reranking may be used to optimize retrieval precision by filtering or down-weighting blocks that fall below a predefined relevance threshold, maintaining that only blocks with strong alignment to the modified prompt representation are used for generating the response. In some embodiments, reranking may be integrated with an adaptive retrieval feedback mechanism, wherein retrieval conditions are dynamically adjusted based on previous reranking effectiveness, maintaining that future retrieval processes are optimized for relevance. These and other reranking methodologies may be used alone or in combination to enhance retrieval-augmented response generation by prioritizing the most contextually relevant selected blocks in relation to the prompt embedding vector.

Some embodiments may then generate a response 130 using a generative AI model. The response may be based on one or more of the selected blocks from the data set, the original prompt provided, or the modified prompt embedding vector, where different embodiments may utilize these sources independently or in various combinations. In some embodiments, the response may be generated using only the selected blocks, wherein the generative AI model is conditioned strictly on the retrieved content without considering the original prompt beyond its role in retrieval. In other embodiments, the response may be generated based on both the selected blocks and the original prompt, wherein the generative AI model incorporates the prompt's linguistic structure, intent, or contextual framing in addition to the information retrieved from the data set. In some embodiments, the response may be generated based on the modified prompt embedding vector without direct reliance on retrieved blocks or the original prompt text, wherein the model utilizes the transformed representation to guide response generation. Some embodiments may utilize all available sources in combination, wherein the response is conditioned on the original prompt, the selected blocks, and the modified prompt embedding vector, allowing the system to balance retrieved content with query-level contextualization.

The generative AI model used to generate the response may be a large language model (LLM), wherein the model comprises a deep neural network trained on vast corpora of text data to learn probabilistic distributions over word sequences and linguistic structures. In some embodiments, the generative AI model may be an autoregressive transformer-based model, such as GPT-based architectures, wherein the model generates text sequentially by predicting the most probable next token given an input context. The response generation process may involve sampling from the model's learned probability distribution, using techniques such as temperature scaling, nucleus sampling, or beam search to balance fluency and diversity in the output. In some embodiments, the generative AI model may be a sequence-to-sequence model, such as those based on encoder-decoder architectures, wherein an input sequence is processed into a latent representation, and a decoder network subsequently generates a response conditioned on that representation.

In some embodiments, alternative AI models may be used for response generation, including retrieval-augmented models that perform ranking and synthesis rather than direct sequence generation. In some embodiments, the generative AI model may employ reinforcement learning techniques, wherein response generation is optimized based on reward signals derived from human feedback, retrieval consistency, or externally defined quality metrics. Some embodiments may utilize hybrid approaches, wherein the response is generated using both a statistical retrieval model and a neural text generator, such as a model that selects pre-existing text passages while supplementing gaps using a language model. In some embodiments, the generative AI model may be a knowledge graph-driven response system, wherein structured data representations inform text generation to support factual accuracy and domain-specific coherence. In some embodiments, the model may be adapted for multi-modal generation, wherein textual responses are generated alongside image, audio, or structured output based on cross-modal embeddings. These and other variations may be used depending on system constraints, application-specific requirements, and optimization goals related to response fidelity, retrieval accuracy, and generative flexibility.

In some embodiments, the accuracy and fidelity of the generated response may be assessed. Some embodiments may include deciding whether the response meets a fidelity threshold. A fidelity threshold may represent a predefined or dynamically computed criterion that evaluates how well the generated response aligns with retrieved data, user intent, or external validation sources. The fidelity threshold may be defined using a variety of computational techniques, including semantic similarity measurements, response attribution analysis, and external knowledge verification.

In some embodiments, a fidelity threshold may be set as a static value, wherein responses are required to achieve a minimum similarity score when compared against retrieved data blocks, such as a cosine similarity score exceeding a predetermined threshold. In some embodiments, the fidelity threshold may be defined dynamically, wherein it is adjusted based on contextual factors, such as the complexity of the input prompt, the diversity of retrieved content, or prior response success rates. A dynamically computed fidelity threshold may be determined using machine learning models trained to predict response confidence based on retrieval distribution, generative coherence, and external validation signals. Some embodiments may incorporate reinforcement learning techniques wherein the fidelity threshold is iteratively optimized based on historical retrieval success rates and response evaluations. In some embodiments, an external evaluation mechanism may be used to assess response fidelity, wherein outputs are compared against a ground truth dataset or validated by human review before being accepted as meeting the threshold.

In some embodiments, if it is determined that the generated response fails to meet the fidelity threshold or another accuracy measure, the system may regenerate the modified prompt embedding vector and reprocess the method until a response is generated that satisfies the fidelity criteria. This iterative process may involve adjusting the prompt representation within the embedding space, refining the retrieval selection process, or altering the method of response generation to optimize alignment with the retrieved data. In some embodiments, the system may apply query expansion techniques or reformulate the prompt dynamically to improve retrieval performance before generating a new response. In some embodiments, a reinforcement learning model may be used to adjust the prompt embedding modification process based on the previous failure, maintaining that subsequent retrievals and generations move toward meeting the fidelity threshold.

In some embodiments, if a response does not meet the fidelity or accuracy threshold, the system may prompt the user to supply additional information, refine the input prompt, or provide clarifications that may improve retrieval and response quality. This may include user-provided constraints, selection of preferred retrieved sources, or manual adjustments to the generated response. In some embodiments, an interactive user interface may guide users through iterative refinements, allowing them to modify or restructure their input to achieve higher-fidelity responses.

In some embodiments, if the system determines that it is unable to generate a response that meets the required level of accuracy or fidelity despite multiple iterations, it may generate a message or error notification stating that it was unable to fulfill the request. This message may include diagnostic information such as retrieval failure reasons, response coherence issues, or insufficient retrieved data coverage. In some embodiments, the system may suggest alternative queries or provide recommendations for improving retrieval precision to enhance response fidelity in future attempts.

In some embodiments, accuracy and fidelity of the generated response may be assessed using alternative methodologies that do not rely on a predefined fidelity threshold. One such approach involves cross-validation against multiple retrieval results, wherein the generated response is compared to a set of retrieved blocks to determine whether the response appropriately integrates or reflects the information contained in different sources. This method may involve checking for consistency between the generated response and retrieved blocks by maintaining that key factual elements, numerical data, or named entities align across multiple retrieved sources. In some embodiments, a divergence metric such as Kullback-Leibler divergence or Jensen-Shannon divergence may be used to measure the information distribution between retrieved content and the generated response, wherein significant divergence indicates that the response may contain hallucinated or extraneous information.

Another method for assessing fidelity and accuracy involves linguistic coherence and logical consistency analysis, wherein the generated response is evaluated for internal contradictions, incomplete reasoning, or structurally illogical statements. In some embodiments, a logic consistency model may be used to check whether the generated response maintains a coherent structure that logically follows from the retrieved blocks, maintaining that retrieved facts are not misrepresented or taken out of context. In some embodiments, natural language inference models may be employed to determine whether the generated response entails, contradicts, or is neutral with respect to the retrieved content. If the response is determined to be logically inconsistent with the provided information, the system may flag it for review or initiate a regeneration process.

In some embodiments, accuracy and fidelity may be assessed by measuring attribution strength within the generated response. This process may involve analyzing token-level or phrase-level attribution using an attribution propagation mechanism, wherein each segment of the response is mapped to its corresponding retrieved block. If a significant portion of the response cannot be directly traced to any retrieved content, it may indicate potential hallucination or fabrication. In some embodiments, the response may be assigned an attribution confidence score, where a lower confidence score suggests that portions of the response rely too heavily on the generative model's pre-trained knowledge rather than the retrieved blocks. In some embodiments, attention-based alignment models may be used to determine whether higher attention weights were placed on relevant retrieved content during response generation, with lower-weighted attributions suggesting weaker fidelity to the retrieved blocks.

In some embodiments, factual accuracy may be evaluated by comparing the generated response to an external knowledge base or structured data repository to determine whether key facts align with established information sources. In some embodiments, structured query generation techniques may be used to extract fact-based elements from the generated response and compare them against ground truth databases, such as legal case archives, financial records, or scientific publications. If discrepancies are detected between the generated response and authoritative sources, the system may either reprocess the query, highlight potential inconsistencies for user review, or adjust retrieval selection criteria. Some embodiments may integrate fact-checking models trained on validated datasets, wherein retrieved facts are cross-referenced against known factual statements, and conflicting or unverifiable claims in the generated response may be flagged for further inspection.

In some embodiments, accuracy and fidelity may be assessed through multi-step response validation, wherein the generated response undergoes iterative refinement and self-verification processes. In such embodiments, an initial response may be generated and then used as a secondary input prompt to a validation model, which attempts to rederive the response from retrieved content. If the re-derived response significantly deviates from the original output, it may indicate instability in the response generation process or overreliance on generative patterns rather than retrieved data. Some embodiments may employ adversarial validation, wherein a separate model is tasked with identifying weaknesses, inconsistencies, or speculative content within the response. If the validation model detects anomalies, the system may flag the response for regeneration or further refinement.

These and other methodologies for assessing accuracy and fidelity may be used alone or in combination to support that the generated response maintains a high degree of trustworthiness, alignment with retrieved information, and coherence across different applications of retrieval-augmented generative AI. The selection of an appropriate validation method may depend on factors such as the nature of the dataset, the specific requirements of the retrieval process, or the desired degree of interpretability and transparency in response generation.

Some embodiments may quantify an amount of influence that the selected blocks have on the generated response 135. The quantified amount of influence may be depicted as a numerical value, such as a percentage, wherein each selected block is assigned a proportion of contribution to the final response relative to other retrieved blocks. In some embodiments, the quantified amount of influence may be represented using a weighted contribution score, wherein each block is assigned a normalized weight based on its impact on different segments of the generated response. In some embodiments, the quantified amount of influence may be represented as a probability distribution over the selected blocks, wherein each block's influence is expressed as the likelihood that it contributed to specific generated text sequences. Some embodiments may use a graphical or heatmap-based representation, wherein portions of the response text are visually annotated with influence indicators corresponding to the retrieved blocks from which the content was derived. In some embodiments, a confidence interval may be assigned to each influence measurement, allowing the system to express the degree of certainty regarding each block's contribution to the response. In some embodiments, the influence of each block may be represented in terms of its positional impact, wherein retrieval order or hierarchical contribution weightings are applied to assess whether blocks appearing earlier in the response generation process exert a stronger influence than those retrieved later.

In some embodiments, quantifying the amount of influence may include various calculations to provide a numerical value reflecting the contribution of each selected block to the generated response. Some embodiments may compute a model loss value in a scenario where the respective data block is removed from the selected data blocks, wherein the impact of its removal on the model's output confidence is measured to assess its relative influence. In some embodiments, an attenuation weight may be assigned to each retrieved block, wherein attenuation is computed based on the degree to which information from the block is preserved or diminished in the final response, allowing for the differentiation between high-impact and low-impact blocks. Some embodiments may quantify influence using a log-odds score, wherein the change in probability distribution over response token generation is assessed based on the presence or absence of each retrieved block, allowing for the estimation of whether retrieved content significantly alters word choice or structure within the generated text. In some embodiments, a likelihood ratio may be calculated to compare the probability of generating the response given the retrieved blocks versus the probability of generating the response in the absence of those blocks, wherein a higher ratio indicates a greater dependence on the retrieved content for response generation. These and other calculations may be used alone or in combination to generate an interpretable influence measure that reflects the relationship between selected blocks and generated outputs, facilitating transparency in retrieval-augmented response generation.

In some embodiments, quantifying the influence of each selected block on the generated response may be performed using an embedding similarity-based influence method, wherein text from the selected blocks and the generated response is mapped into a multi-dimensional vector space. In some embodiments, the process may begin with determining a numerical representation of each selected block by mapping the text of the block into an embedding space. This transformation may be performed using a trained neural network embedding model, wherein the embedding model converts the textual content into a high-dimensional vector that preserves semantic relationships between words, phrases, and concepts. The embedding model may be trained on domain-specific data or optimized for retrieval tasks to support that representations capture relevant contextual information. Each selected block from the data set is mapped into this embedding space, resulting in a set of vectorized representations that can be used for proximity-based comparisons. In some embodiments, the generated response is also mapped into the same embedding space, wherein each portion of the response is represented as a numerical vector. The embedding transformation for the generated response may use the same embedding model as the selected blocks to maintain consistency in representation. The response embedding may be computed at multiple granularities, such as sentence-level, phrase-level, or token-level representations, depending on the required resolution for influence quantification. In some embodiments, the response embedding process may be performed iteratively, wherein response segments are processed in relation to the selected blocks to refine the alignment of influence attribution. The system may then associate individual portions of the generated response with corresponding portions of the selected blocks based on their proximity within the embedding space. In some embodiments, this proximity determination may be computed using cosine similarity, Euclidean distance, or other vector distance metrics that measure how closely response segments align with retrieved blocks. The association process may involve segmenting the response into discrete textual units, wherein each unit is linked to the most similar retrieved block based on vector similarity. In some embodiments, overlapping associations may be allowed, wherein a response segment may be influenced by multiple retrieved blocks based on distributed similarity weightings.

In some embodiments, after associating response portions with selected blocks, the system may compute a measure of contribution for each selected block by aggregating proximity values between its numerical representation and the numerical representations of the associated portions of the generated response. This aggregation process may involve summing or averaging the similarity scores across all relevant response segments to produce a single influence score for each selected block. In some embodiments, weighting factors may be applied to emphasize contributions based on retrieval confidence, response structure, or linguistic coherence. In some embodiments, influence scores may be adjusted using a scaling function that accounts for variations in retrieval effectiveness, maintaining that influence attribution remains consistent across different queries and response conditions. Once the contribution measures for each selected block have been computed, the system may normalize the influence scores across all selected blocks to maintain that the total influence values satisfy predefined constraints. In some embodiments, normalization may be performed using L1 normalization, wherein the sum of all influence scores across retrieved blocks is constrained to a fixed value, such as 1, maintaining that influence scores are interpretable as probability distributions. In some embodiments, alternative normalization techniques such as softmax scaling or percentile-based standardization may be applied to refine influence quantification based on the distribution of similarity scores.

In some embodiments, influence may be quantified using an attention-based influence attribution method, wherein attention weights within the generative AI model are analyzed to determine the extent to which each retrieved block influenced the generation of specific portions of the response. Attention-based influence may be computed by extracting cross-attention scores from the transformer layers of the generative model, wherein higher attention weights assigned to specific retrieved blocks indicate stronger influence on response formation. In some embodiments, attention scores may be aggregated across multiple layers and attention heads to generate a holistic contribution score for each block. In some embodiments, influence quantification may be refined by applying attention normalization techniques that account for positional biases in attention distributions, maintaining that retrieved blocks are fairly weighted regardless of their position in the input sequence. Some embodiments may further incorporate residual attention tracking, wherein attention-based influence is computed over iterative response generation steps to capture long-range dependencies between retrieved content and generated text.

In some embodiments, influence quantification may be performed using a gradient-based influence method, wherein the effect of each retrieved block on the response generation process is assessed by computing gradient-based sensitivity measures. Gradient-based influence quantification involves determining how small perturbations in the input embeddings of retrieved blocks affect the model's output probabilities or response structure. In some embodiments, influence may be estimated using Integrated Gradients, wherein the contribution of each retrieved block is computed by integrating the gradient of the response output with respect to the input embedding of the block along a linear path from a baseline state to the actual embedding representation. In some embodiments, influence may be assessed using Saliency Maps, wherein high-gradient regions in the embedding space indicate retrieved blocks that had a strong influence on token selection in the generated response. Some embodiments may apply SmoothGrad techniques, wherein multiple perturbed versions of the input embeddings are sampled, and influence is computed as the averaged gradient effect across these perturbed samples to reduce noise and enhance attribution stability.

In some embodiments, influence quantification may be determined using a perturbation-based influence method, wherein the contribution of each retrieved block is measured by systematically removing or altering blocks and observing the effect on response generation. In some embodiments, influence may be estimated by generating a response with all selected blocks included and then generating additional responses where individual retrieved blocks are omitted one at a time. The change in response content or output probability distribution between the original response and the perturbed responses provides a measure of the removed block's influence. In some embodiments, influence quantification may involve computing a response divergence metric, such as the Kullback-Leibler divergence or Jensen-Shannon divergence, between the probability distributions of token predictions in the original and perturbed responses, wherein larger divergence values indicate stronger reliance on the removed block. Some embodiments may apply Shapley Value Attribution, wherein retrieved blocks are selectively removed in various combinations to compute their marginal contribution to response generation, maintaining that influence attribution accounts for interactions between multiple retrieved blocks.

These and other influence quantification methodologies may be used alone or in combination, wherein different methods may be preferred based on the structure of the generative AI system, the required level of attribution detail, and computational efficiency considerations. In some embodiments, a hybrid influence quantification framework may be implemented, wherein multiple influence measures are combined using an ensemble-based approach to improve accuracy and robustness. In some embodiments, different influence methods may be dynamically selected based on query complexity, retrieval confidence, or domain-specific retrieval constraints to optimize transparency and interpretability in retrieval-augmented response generation.

In some embodiments, a representation of the amount of influence of the selected blocks on the generated response may be created. This representation may be created and supplied to a user as an output or may be generated and utilized for further training purposes. In some embodiments, the representation can include associations between the selected blocks and the corresponding portions of the generated response to indicate which portions of the response are directly tied to and influenced by individual blocks that were selected as being proximate with the prompt embedding vector representation. In some embodiments, the representation may include values attributed to the individually selected blocks, where each value represents a measure of contribution of that block to a corresponding portion of the response.

In some embodiments, the representation of influence may also include confidence scores that indicate the system's certainty regarding the computed influence values, wherein confidence may be derived from retrieval ranking stability, embedding similarity variance, or response token generation probabilities. In some embodiments, the representation may include weights derived from the retrieval process, wherein blocks retrieved with higher priority due to relevance-ranking algorithms may be assigned different influence weightings compared to blocks retrieved at lower ranks. In some embodiments, the representation may include error margins or statistical measures indicating the potential variance in influence quantification due to stochastic elements in the generative AI process. Some embodiments may incorporate contextual metadata, such as time-based retrieval relevance, document sourcing history, or provenance indicators, to provide additional interpretability to the quantified influence representation.

In some embodiments, the representation may include data or instructions that may be used to generate a graphical user interface that maps response text segments to corresponding retrieved sources. In some embodiments, this may be performed using provenance-tracking visualization, wherein a system provides an interactive display that visually links different portions of the generated response to the selected blocks that contributed to their generation. Provenance-tracking visualization may involve color-coded highlights, annotation overlays, or interactive tooltips that allow a user to examine how different retrieved blocks influenced different sections of the generated response. In some embodiments, the visualization may be structured as a dependency graph, wherein response segments are represented as nodes connected to their contributing retrieved blocks, allowing for an intuitive understanding of multi-source attribution.

In some embodiments, the visualization may include influence heatmaps, wherein sections of the generated response are overlaid with visual intensity indicators corresponding to the influence score of each retrieved block, allowing users to quickly discern which retrieved sources had the greatest effect on specific parts of the response. Some embodiments may utilize layered visualization techniques, wherein different types of influence measures, such as embedding similarity-based influence, attention-based influence, or gradient-based influence, are represented using distinct visual elements to provide a comprehensive view of attribution. In some embodiments, the visualization may be interactive, allowing users to filter retrieved sources based on influence thresholds, highlight specific retrieval contributions, or compare alternative retrieval-based responses side by side. Some embodiments may incorporate clickable citations, wherein individual response segments are linked to their associated retrieved documents or original data sources, allowing users to trace AI-generated content back to its provenance in a transparent manner.

Figure 2:
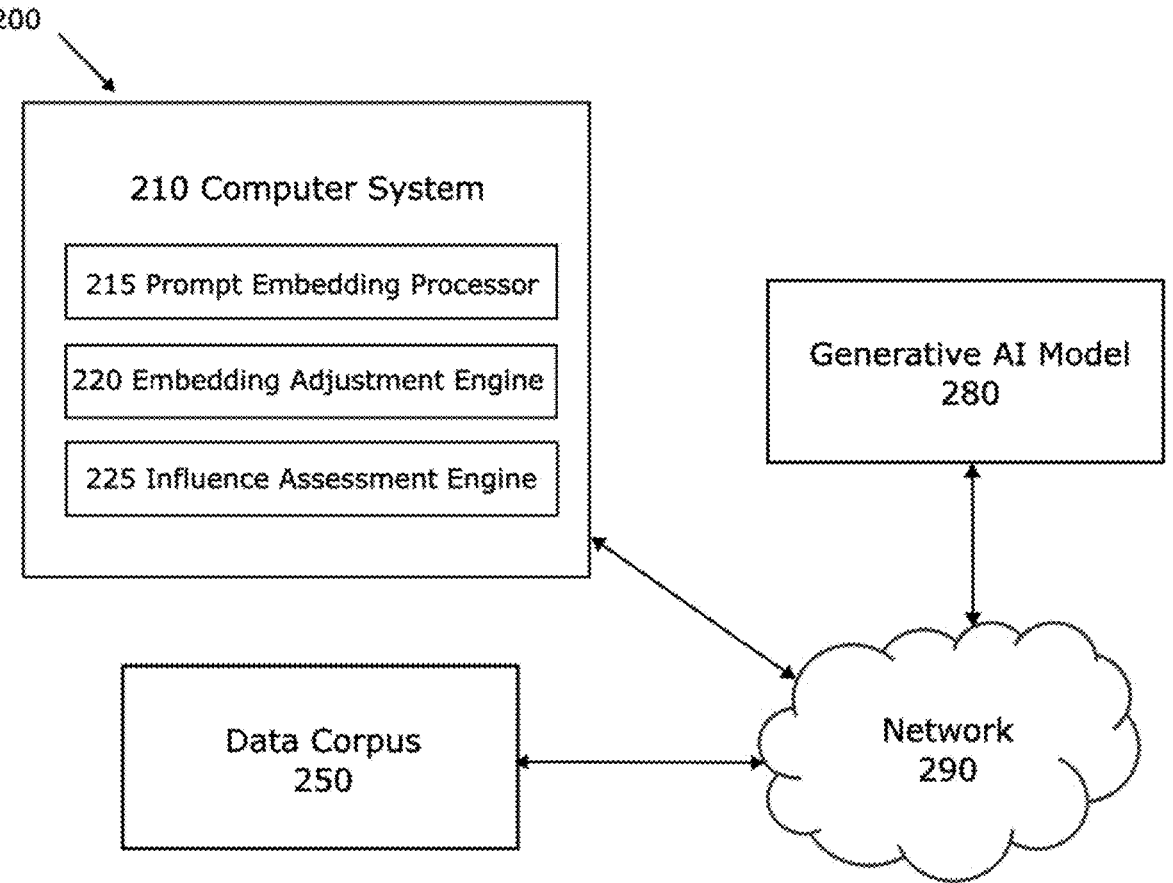
FIG. 2 illustrates an exemplary system architecture for enhancing retrieval augmented generation accuracy.

FIG. 2 is a diagram that illustrates an exemplary system architecture 200 consistent with some embodiments. The system may perform the method of FIG. 1 and may be implemented with computing devices like that shown in FIG. 3 in some cases. The system architecture 200 includes a computer system 210, a data corpus 250, a generative AI model 280, and a network 290. The computer system 210 may perform executing retrieval and response augmentation tasks (e.g., using one or more of the computing devices of FIG. 3), while the data corpus 250 may function as an external knowledge repository from which relevant information is retrieved. The generative AI model 280 may be responsible for generating responses, incorporating both retrieved content and contextual processing. The network 290 may facilitate communication between these components.

The computer system 210 may comprise multiple functional components that collectively facilitate prompt modification, retrieval augmentation, and influence quantification. Within the computer system 210, a prompt embedding processor 215 may be responsible for processing the input prompt and converting it into an embedding representation within a multi-dimensional embedding space. The embedding adjustment engine 220 may be configured to modify a prompt embedding vector to optimize retrieval performance by aligning it with relevant data blocks from the data corpus 250. The influence assessment engine 225 may evaluate the contribution of retrieved data blocks to the final generated response, quantifying the degree to which retrieved content informs the generated output.

In some embodiments, the computer system 210 may communicate with the data corpus 250 and the generative AI model 280 via the network 290, which may be implemented as a local area network, a wide area network, the Internet, or a cloud-based distributed computing infrastructure. The network 290 may allow retrieval requests to be transmitted to the data corpus 250, where selected data blocks are identified and returned to the computer system 210. The network connection may facilitate data exchange with the generative AI model 280, allowing the system to transmit modified prompts, receive generated responses, and refine output generation based on retrieved content. In some embodiments, network communications may involve encrypted data transmission, distributed data storage protocols, or parallel processing across multiple remote nodes, depending on system design and deployment constraints.

Some embodiments may integrate one or more components of the system architecture 200 within the computer system 210, rather than implementing them as separate entities connected via the network 290. In some embodiments, the data corpus 250, the generative AI model 280, or both may be incorporated into the computer system 210, which may reduce retrieval latency, improve security by limiting external data transmissions, optimize computational efficiency, and, in some cases, allow for offline operation in environments where network access may be limited or unreliable.

In some embodiments, the data corpus 250 may be stored within the computer system 210, wherein the corpus may be maintained as an internal database, indexed document repository, or structured knowledge store. The computer system 210 may, in some implementations, index text blocks and store precomputed embeddings within local memory or a dedicated storage unit, allowing retrieval operations to be performed without relying on remote data access. In some embodiments, a locally stored corpus may be periodically synchronized with external databases, maintaining that the retrieved information remains up to date. Some embodiments may involve a hybrid approach, wherein frequently accessed or high-priority data is stored locally while less frequently accessed data remains in a remote storage system, allowing for a balance between retrieval speed and data availability.

In some embodiments, the generative AI model 280 may be implemented within the computer system 210, wherein the model may be stored and executed locally rather than accessed as a remote service over the network 290. Some embodiments may involve deploying a transformer-based model, such as a fine-tuned language model stored in system memory or specialized hardware, while others may use a lightweight model designed for on-device inference. In some implementations, the computer system 210 may incorporate hardware accelerators, such as graphics processing units, tensor processing units, or custom AI inference chips, to optimize the performance of locally executed generative models. Some embodiments may use quantized or pruned versions of large-scale language models to reduce computational overhead while maintaining response quality.

In some embodiments, both the data corpus 250 and the generative AI model 280 may be integrated within the computer system 210, allowing for a self-contained retrieval and response generation process. This configuration may be beneficial for applications involving edge computing, secure environments, or air-gapped systems where external network access is restricted. In some implementations, the system may periodically update the data corpus 250 by ingesting new documents or dynamically adapting its indexed retrieval data based on user interactions. Some embodiments may implement an on-device training loop, wherein the generative AI model is incrementally fine-tuned on newly ingested data without requiring external retraining. In some implementations, federated learning techniques may be used to allow multiple instances of the computer system 210 to share learned model updates without transmitting raw data over the network 290.

Alternative embodiments may integrate one or more components of the system architecture 200 within the computer system 210, rather than implementing them as separate entities connected via the network 290. In some embodiments, the data corpus 250, the generative AI model 280, or both may be incorporated into the computer system The computer system 210 may include various components responsible for processing prompts, modifying embeddings, retrieving data, and quantifying the influence of retrieved content on the generated response. In some embodiments, the computer system 210 may include a prompt embedding processor 215, an embedding adjustment engine 220, and an influence assessment engine 225, each of which may perform specific functions to facilitate retrieval-augmented response generation. These components may operate sequentially or in parallel, depending on system architecture, optimization constraints, and computational efficiency considerations.

The prompt embedding processor 215 may perform operations related to converting a received prompt into an embedding representation within a multi-dimensional embedding space. In some embodiments, the prompt embedding processor 215 may process the input prompt, wherein the textual content is segmented into discrete units that facilitate embedding computation. Some embodiments may preprocess the prompt by normalizing text, removing stop words, expanding abbreviations, or applying text cleaning techniques before encoding. The processor may then map the prompt to a numerical representation using a pre-trained embedding model, such as a transformer-based language model, a word embedding model, or a domain-specific vectorization method. In some implementations, the prompt embedding processor 215 may incorporate contextual information from prior user queries, session history, or document metadata to refine the embedding representation. In some embodiments, the processor may adjust embedding parameters dynamically, wherein additional weighting factors are applied to specific elements of the vector representation based on retrieval goals, prior retrieval success rates, or predefined optimization criteria.

The embedding adjustment engine 220 may modify the prompt embedding vector to optimize retrieval performance by shifting the representation within the embedding space. In some embodiments, the embedding adjustment engine 220 may apply transformation operations to adjust proximity relationships between the prompt embedding and candidate retrieval blocks within the data corpus 250. Some implementations may perform scalar adjustments, wherein individual dimensions of the embedding vector are reweighted or rescaled to emphasize or suppress certain features that influence retrieval ranking. In some embodiments, the engine may modify the embedding vector by applying a learned transformation function, such as a neural network-based projection model, wherein the transformation is optimized to improve alignment with semantically relevant retrieval candidates. Some embodiments may perform vector perturbation, wherein controlled variations are introduced to the embedding representation to explore alternative retrieval pathways while maintaining contextual integrity. In some implementations, the embedding adjustment engine 220 may incorporate external retrieval feedback, wherein retrieval success rates, document ranking histories, or user interactions are used to refine transformation parameters dynamically.

The influence assessment engine 225 may quantify the contribution of selected retrieval blocks to the final generated response by computing an influence score for each block. In some embodiments, the influence assessment engine 225 may determine the degree of contribution of each block by comparing its embedding representation to the generated response using similarity metrics such as cosine similarity, Euclidean distance, or probabilistic attribution measures. Some implementations may compute influence using attention-based attribution, wherein attention weight distributions from the generative AI model 280 are analyzed to determine which retrieved blocks received the highest weighting during response formation. In some embodiments, influence may be quantified using gradient-based sensitivity analysis, wherein changes in the response prediction distribution are measured when selected blocks are perturbed or removed from retrieval input. Some implementations may use perturbation-based influence quantification, wherein alternative responses are generated with and without individual blocks, and the resulting variations in generated text are analyzed to determine the degree of reliance on specific retrieval content. In some embodiments, the influence assessment engine 225 may aggregate influence scores across multiple retrieved blocks to generate a contribution ranking, wherein the blocks with the highest influence scores are highlighted for interpretability or response validation purposes.

The data corpus 250 may comprise a collection of information used to retrieve relevant content for augmenting response generation, wherein the data may be structured, semi-structured, or unstructured. In some embodiments, the data corpus 250 may contain natural language text documents, structured datasets, multimodal data, dynamically updated data sources, and data in other formats. Some embodiments may include more than 10,000 such documents, wherein the corpus size may vary depending on the specific implementation and domain requirements. In some embodiments, the data corpus 250 may also contain struc-tured datasets, such as relational databases, knowledge graphs, or tabular data, wherein retrieval may involve querying structured elements rather than full-text search. Some implementations may incorporate multimodal data, wherein text-based retrieval is supplemented with image data, audio transcripts, video metadata, or sensor-generated logs. In some embodiments, the data corpus 250 may include dynamically updated data sources, such as real-time streaming feeds, periodically refreshed regulatory databases, or indexed web content that evolves over time. In some implementations, different sections of the data corpus may be assigned varying levels of retrieval priority, wherein high-confidence sources such as peer-reviewed literature or official regulatory documents are weighted more heavily in retrieval ranking than user-generated content or lower-confidence sources. The organization and indexing of the data corpus 250 may vary across embodiments, wherein some implementations may store documents as raw text, others may apply vector-based indexing for efficient retrieval, and some may use a combination of hierarchical and keyword-based indexing to optimize retrieval latency and relevance.

The generative AI model 280 may comprise a machine learning model configured to generate responses based on input prompts, retrieved data, prompt embedding vectors, or a combination thereof. In some embodiments, the generative AI model 280 may be a transformer-based neural network trained on large-scale corpora to generate coherent and contextually relevant text. Some embodiments may utilize an autoregressive language model, wherein the model generates text sequentially by predicting the most probable next token given the preceding context. In some implementations, the generative AI model 280 may include a sequence-to-sequence model, wherein an encoder processes the input, and a decoder generates the response based on a latent representation of the processed input. Some embodiments may use retrieval-augmented generation techniques, wherein the model integrates retrieved data blocks into the response by conditioning its output on the retrieved content. In some implementations, the generative AI model 280 may be fine-tuned for specific domains, such as legal analysis, medical diagnostics, or scientific research, wherein domain-specific knowledge is incorporated into the model's pre-training or retrieval augmentation pipeline. Some embodiments may apply reinforcement learning techniques to refine the response generation process based on feedback from retrieval effectiveness, user interactions, or external validation sources. In some implementations, the generative AI model 280 may include mechanisms for response validation, such as confidence scoring, attribution tracking, or hallucination detection, wherein generated responses are assessed for factual accuracy and alignment with retrieved content. Some embodiments may further incorporate multi-modal capabilities, wherein the generative AI model 280 processes not only text but also other data formats such as images, audio, or structured data representations.

Figure 3:
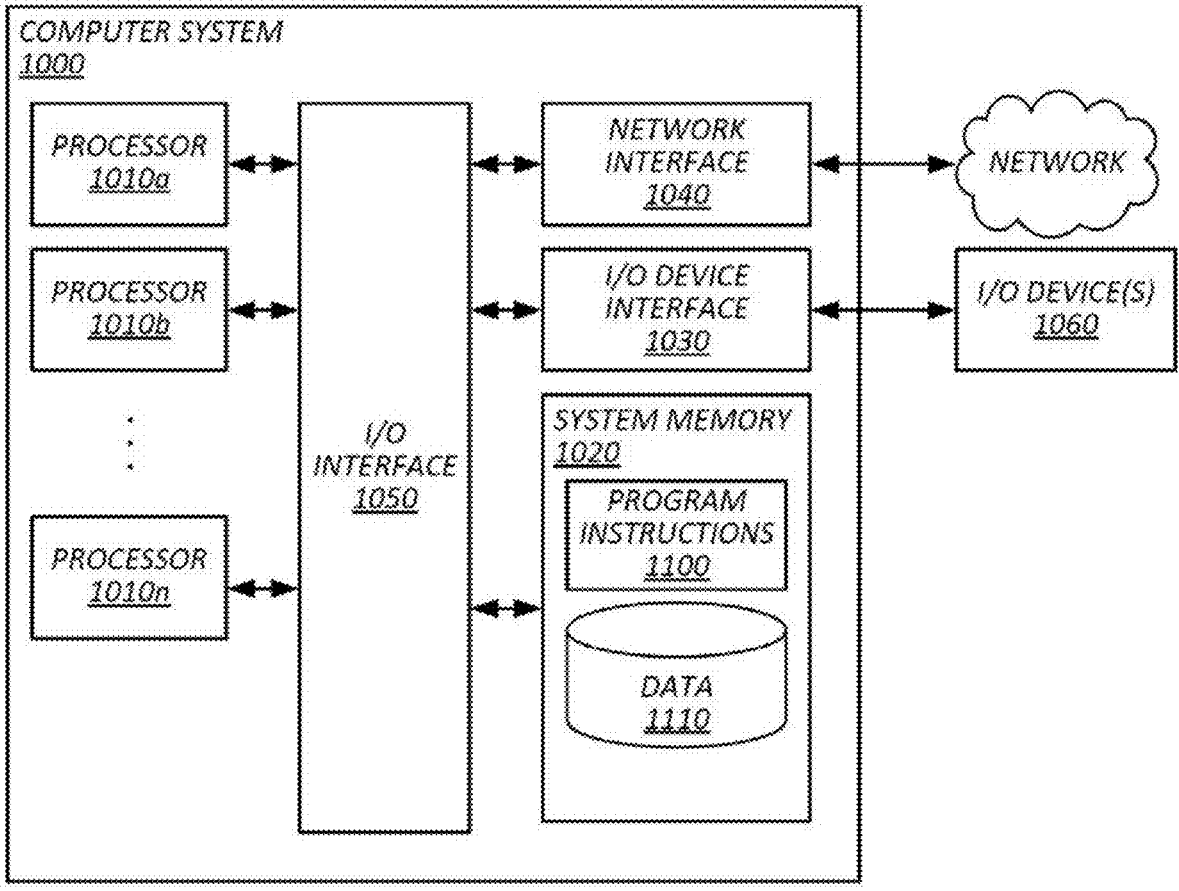
FIG. 3 illustrates a computer system configured to execute the method for enhancing retrieval augmented generation accuracy.

FIG. 3 is a diagram that illustrates an exemplary computing system 1000 in accordance with embodiments of the present technique. A single computing device is shown, but some embodiments of a computer system may include multiple computing devices that communicate over a network, for instance in the course of collectively executing various parts of a distributed application. Various portions of systems and methods described herein may include or be executed on one or more computer systems similar to computing system 1000. Further, processes and modules described herein may be executed by one or more processing systems similar to that of computing system 1000.

Computing system 1000 may include one or more processors (e.g., processors 1010*a*-1010*n*) coupled to system memory 1020, an input/output I/O device interface 1030, and a network interface 1040 via an input/output (I/O) interface 1050. A processor may include a single processor or a plurality of processors (e.g., distributed processors). A processor may be any suitable processor capable of executing or otherwise performing instructions. A processor may include a central processing unit (CPU) that carries out program instructions to perform the arithmetical, logical, and input/output operations of computing system 1000. A processor may execute code (e.g., processor firmware, a protocol stack, a database management system, an operating system, or a combination thereof) that creates an execution environment for program instructions. A processor may include a programmable processor. A processor may include general or special purpose microprocessors. A processor may receive instructions and data from a memory (e.g., system memory 1020). Computing system 1000 may be a uni-processor system including one processor (e.g., processor 1010*a*), or a multi-processor system including any number of suitable processors (e.g., 1010*a*-1010*n*). Multiple processors may be employed to provide for parallel or sequential execution of one or more portions of the techniques described herein. Processes, such as logic flows, described herein may be performed by one or more programmable processors executing one or more computer programs to perform functions by operating on input data and generating corresponding output. Processes described herein may be performed by, and apparatus can also be implemented as, special purpose logic circuitry, e.g., an FPGA (field programmable gate array) or an ASIC (application specific integrated circuit). Computing system 1000 may include a plurality of computing devices (e.g., distributed computer systems) to implement various processing functions.

I/O device interface 1030 may provide an interface for connection of one or more I/O devices 1060 to computer system 1000. I/O devices may include devices that receive input (e.g., from a user) or output information (e.g., to a user). I/O devices 1060 may include, for example, graphical user interface presented on displays (e.g., a cathode ray tube (CRT) or liquid crystal display (LCD) monitor), pointing devices (e.g., a computer mouse or trackball), keyboards, keypads, touchpads, scanning devices, voice recognition devices, gesture recognition devices, printers, audio speakers, microphones, cameras, or the like. I/O devices 1060 may be connected to computer system 1000 through a wired or wireless connection. I/O devices 1060 may be connected to computer system 1000 from a remote location. I/O devices 1060 located on remote computer system, for example, may be connected to computer system 1000 via a network and network interface 1040.

Network interface 1040 may include a network adapter that provides for connection of computer system 1000 to a network. Network interface 1040 may facilitate data exchange between computer system 1000 and other devices connected to the network. Network interface 1040 may support wired or wireless communication. The network may include an electronic communication network, such as the Internet, a local area network (LAN), a wide area network (WAN), a cellular communications network, or the like.

System memory 1020 may be configured to store program instructions 1100 or data 1110. Program instructions 1100 may be executable by a processor (e.g., one or more of processors 1010*a*-1010*n*) to implement one or more embodiments of the present techniques. Instructions 1100 may include modules of computer program instructions for implementing one or more techniques described herein with regard to various processing modules. Program instructions may include a computer program (which in certain forms is known as a program, software, software application, script, or code). A computer program may be written in a programming language, including compiled or interpreted languages, or declarative or procedural languages. A computer program may include a unit suitable for use in a computing environment, including as a stand-alone program, a module, a component, or a subroutine. A computer program may or may not correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one or more computer processors located locally at one site or distributed across multiple remote sites and interconnected by a communication network.

System memory 1020 may include a tangible program carrier having program instructions stored thereon. A tangible program carrier may include a non-transitory computer readable storage medium. A non-transitory computer readable storage medium may include a machine-readable storage device, a machine-readable storage substrate, a memory device, or any combination thereof. Non-transitory computer readable storage medium may include non-volatile memory (e.g., flash memory, ROM, PROM, EPROM, EEPROM memory), volatile memory (e.g., random access memory (RAM), static random access memory (SRAM), synchronous dynamic RAM (SDRAM)), bulk storage memory (e.g., CD-ROM and/or DVD-ROM, hard-drives), or the like. System memory 1020 may include a non-transitory computer readable storage medium that may have program instructions stored thereon that are executable by a computer processor (e.g., one or more of processors 1010*a*-1010*n*) to cause the subject matter and the functional operations described herein. A memory (e.g., system memory 1020) may include a single memory device and/or a plurality of memory devices (e.g., distributed memory devices). Instructions or other program code to provide the functionality described herein may be stored on a tangible, non-transitory computer readable media. In some cases, the entire set of instructions may be stored concurrently on the media, or in some cases, different parts of the instructions may be stored on the same media at different times.

I/O interface 1050 may be configured to coordinate I/O traffic between processors 1010*a*-1010*n*, system memory 1020, network interface 1040, I/O devices 1060, and/or other peripheral devices. I/O interface 1050 may perform protocol, timing, or other data transformations to convert data signals from one component (e.g., system memory 1020) into a format suitable for use by another component (e.g., processors 1010*a*-1010*n*). I/O interface 1050 may include support for devices attached through various types of peripheral buses, such as a variant of the Peripheral Component Interconnect (PCI) bus standard or the Universal Serial Bus (USB) standard.

Embodiments of the techniques described herein may be implemented using a single instance of computer system 1000 or multiple computer systems 1000 configured to host different portions or instances of embodiments. Multiple computer systems 1000 may provide for parallel or sequential processing/execution of one or more portions of the techniques described herein.

Those skilled in the art will appreciate that computer system 1000 is merely illustrative and is not intended to limit the scope of the techniques described herein. Computer system 1000 may include any combination of devices or software that may perform or otherwise provide for the performance of the techniques described herein. For example, computer system 1000 may include or be a combination of a cloud-computing system, a data center, a server rack, a server, a virtual server, a desktop computer, a laptop computer, a tablet computer, a server device, a client device, a mobile telephone, a personal digital assistant (PDA), a mobile audio or video player, a game console, a vehicle-mounted computer, or a Global Positioning System (GPS), or the like. Computer system 1000 may also be connected to other devices that are not illustrated or may operate as a stand-alone system. In addition, the functionality provided by the illustrated components may in some embodiments be combined in fewer components or distributed in additional components. Similarly, in some embodiments, the functionality of some of the illustrated components may not be provided or other additional functionality may be available.

Those skilled in the art will also appreciate that while various items are illustrated as being stored in memory or on storage while being used, these items or portions of them may be transferred between memory and other storage devices for purposes of memory management and data integrity. Alternatively, in other embodiments some or all of the software components may execute in memory on another device and communicate with the illustrated computer system via inter-computer communication. Some or all of the system components or data structures may also be stored (e.g., as instructions or structured data) on a computer-accessible medium or a portable article to be read by an appropriate drive, various examples of which are described above. In some embodiments, instructions stored on a computer-accessible medium separate from computer system 1000 may be transmitted to computer system 1000 via transmission media or signals such as electrical, electromagnetic, or digital signals, conveyed via a communication medium such as a network or a wireless link. Various embodiments may further include receiving, sending, or storing instructions or data implemented in accordance with the foregoing description upon a computer-accessible medium. Accordingly, the present techniques may be practiced with other computer system configurations.

In block diagrams, illustrated components are depicted as discrete functional blocks, but embodiments are not limited to systems in which the functionality described herein is organized as illustrated. The functionality provided by each of the components may be provided by software or hardware modules that are differently organized than is presently depicted, for example such software or hardware may be intermingled, conjoined, replicated, broken up, distributed (e.g., within a data center or geographically), or otherwise differently organized. The functionality described herein may be provided by one or more processors of one or more computers executing code stored on a tangible, non-transitory, machine-readable medium. In some cases, notwithstanding use of the singular term "medium," the instructions may be distributed on different storage devices associated with different computing devices, for instance, with each computing device having a different subset of the instructions, an embodiment consistent with usage of the singular term "medium" herein. In some cases, third party content delivery networks may host some or all of the information conveyed over networks, in which case, to the extent information (e.g., content) is said to be supplied or otherwise provided, the information may be provided by sending instructions to retrieve that information from a content delivery network.

The reader should appreciate that the present application describes several independently useful techniques. Rather than separating those techniques into multiple isolated patent applications, applicants have grouped these techniques into a single document because their related subject matter lends itself to economies in the application process. But the distinct advantages and aspects of such techniques should not be conflated. In some cases, embodiments address all of the deficiencies noted herein, but it should be understood that the techniques are independently useful, and some embodiments address only a subset of such problems or offer other, unmentioned benefits that will be apparent to those of skill in the art reviewing the present disclosure. Due to costs constraints, some techniques disclosed herein may not be presently claimed and may be claimed in later filings, such as continuation applications or by amending the present claims. Similarly, due to space constraints, neither the Abstract nor the Summary of the Invention sections of the present document should be taken as containing a comprehensive listing of all such techniques or all aspects of such techniques.

It should be understood that the description and the drawings are not intended to limit the present techniques to the particular form disclosed, but to the contrary, the intention is to cover all modifications, equivalents, and alternatives falling within the spirit and scope of the present techniques as defined by the appended claims. Further modifications and alternative embodiments of various aspects of the techniques will be apparent to those skilled in the art in view of this description. Accordingly, this description and the drawings are to be construed as illustrative only and are for the purpose of teaching those skilled in the art the general manner of carrying out the present techniques. It is to be understood that the forms of the present techniques shown and described herein are to be taken as examples of embodiments. Elements and materials may be substituted for those illustrated and described herein, parts and processes may be reversed or omitted, and certain features of the present techniques may be utilized independently, all as would be apparent to one skilled in the art after having the benefit of this description of the present techniques. Changes may be made in the elements described herein without departing from the spirit and scope of the present techniques as described in the following claims. Headings used herein are for organizational purposes only and are not meant to be used to limit the scope of the description.

As used throughout this application, the word "may" is used in a permissive sense (i.e., meaning having the potential to), rather than the mandatory sense (i.e., meaning must). The words "include," "including," and "includes" and the like mean including, but not limited to. As used throughout this application, the singular forms "a," "an," and "the" include plural referents unless the content explicitly indicates otherwise. Thus, for example, reference to "an element" or "a element" includes a combination of two or more elements, notwithstanding use of other terms and phrases for one or more elements, such as "one or more." The term "or" is, unless indicated otherwise, non-exclusive, i.e., encompassing both "and" and "or." Terms describing conditional relationships, e.g., "in response to X, Y," "upon X, Y,", "if X, Y," "when X, Y," and the like, encompass causal relationships in which the antecedent is a necessary causal condition, the antecedent is a sufficient causal condition, or the antecedent is a contributory causal condition of the consequent, e.g., "state X occurs upon condition Y obtaining" is generic to "X occurs solely upon Y" and "X occurs upon Y and Z." Such conditional relationships are not limited to consequences that instantly follow the antecedent obtaining, as some consequences may be delayed, and in conditional statements, antecedents are connected to their consequents, e.g., the antecedent is relevant to the likelihood of the consequent occurring. Statements in which a plurality of attributes or functions are mapped to a plurality of objects (e.g., one or more processors performing steps A, B, C, and D) encompasses both all such attributes or functions being mapped to all such objects and subsets of the attributes or functions being mapped to subsets of the attributes or functions (e.g., both all processors each performing steps A-D, and a case in which processor 1 performs step A, processor 2 performs step B and part of step C, and processor 3 performs part of step C and step D), unless otherwise indicated. Similarly, reference to "a computer system" performing step A and "the computer system" performing step B can include the same computing device within the computer system performing both steps or different computing devices within the computer system performing steps A and B. Further, unless otherwise indicated, statements that one value or action is "based on" another condition or value encompass both instances in which the condition or value is the sole factor and instances in which the condition or value is one factor among a plurality of factors. Unless otherwise indicated, statements that "each" instance of some collection have some property should not be read to exclude cases where some otherwise identical or similar members of a larger collection do not have the property, i.e., each does not necessarily mean each and every. Limitations as to sequence of recited steps should not be read into the claims unless explicitly specified, e.g., with explicit language like "after performing X, performing Y," in contrast to statements that might be improperly argued to imply sequence limitations, like "performing X on items, performing Y on the X'ed items," used for purposes of making claims more readable rather than specifying sequence. Statements referring to "at least Z of A, B, and C," and the like (e.g., "at least Z of A, B, or C"), refer to at least Z of the listed categories (A, B, and C) and do not require at least Z units in each category. Unless specifically stated otherwise, as apparent from the discussion, it is appreciated that throughout this specification discussions utilizing terms such as "processing," "computing," "calculating," "determining" or the like refer to actions or processes of a specific apparatus, such as a special purpose computer or a similar special purpose electronic processing/computing device. Features described with reference to geometric constructs, like "parallel," "perpendicular/orthogonal," "square," "cylindrical," and the like, should be construed as encompassing items that substantially embody the properties of the geometric construct, e.g., reference to "parallel" surfaces encompasses substantially parallel surfaces. The permitted range of deviation from Platonic ideals of these geometric constructs is to be determined with reference to ranges in the specification, and where such ranges are not stated, with reference to industry norms in the field of use, and where such ranges are not defined, with reference to industry norms in the field of manufacturing of the designated feature, and where such ranges are not defined, features substantially embodying a geometric construct should be construed to include those features within 15% of the defining attributes of that geometric construct. The terms "first," "second," "third," "given" and so on, if used in the claims, are used to distinguish or otherwise identify, and not to show a sequential or numerical limitation. As is the case in ordinary usage in the field, data structures and formats described with reference to uses salient to a human need not be presented in a human-intelligible format to constitute the described data structure or format, e.g., text need not be rendered or even encoded in Unicode or ASCII to constitute text; images, maps, and data-visualizations need not be displayed or decoded to constitute images, maps, and data-visualizations, respectively; speech, music, and other audio need not be emitted through a speaker or decoded to constitute speech, music, or other audio, respectively. Computer implemented instructions, commands, and the like are not limited to executable code and can be implemented in the form of data that causes functionality to be invoked, e.g., in the form of arguments of a function or API call. To the extent bespoke noun phrases (and other coined terms) are used in the claims and lack a self-evident construction, the definition of such phrases may be recited in the claim itself, in which case, the use of such bespoke noun phrases should not be taken as invitation to impart additional limitations by looking to the specification or extrinsic evidence.

In this patent, to the extent any U.S. patents, U.S. patent applications, or other materials (e.g., articles) have been incorporated by reference, the text of such materials is only incorporated by reference to the extent that no conflict exists between such material and the statements and drawings set forth herein. In the event of such conflict, the text of the present document governs, and terms in this document should not be given a narrower reading in virtue of the way in which those terms are used in other materials incorporated by reference.

The present techniques will be better understood with reference to the following enumerated embodiments:

1. A computer-implemented method, comprising:
   obtaining, with a computer system, a prompt that is, or is part of, a request for a generative artificial intelligence (AI) model to generate a response;
   determining, with the computer system, a prompt embedding vector representing the prompt in an embedding space, wherein proximity within the embedding space at least partially corresponds to semantic similarity;
   modifying, with the computer system, the prompt embedding vector using a trained model configured to adjust prompt embedding vectors to decrease proximity to vectors of blocks in a data set from which data is retrieved to augment generation by the generative AI model;
   determining, with the computer system, that the modified prompt embedding vector is within a threshold distance to vectors in the embedding space corresponding to one or more blocks in the data set and, in response, selecting the one or more blocks in the data set;
   generating, with the computer system, a response using the generative AI model based on the selected one or more blocks in the data set;
   quantifying, with the computer system, for each of at least one of the selected blocks, an amount of influence of the respective block on corresponding text in the generated response; and
   providing, with the computer system, the response and a representation of the quantified amount of influence as an output.

2. The method of claim 1, wherein:
   the data set comprises a corpus of more than 10,000 natural language text documents;

modifying comprises changing scalars of the prompt embedding vector;

selecting the one or more blocks comprises selecting chunks of the natural language text documents; and the embedding space has more than 256 dimensions.

3. The computer-implemented method of claim 1, wherein the trained model configured to adjust prompt embedding vectors is trained by:

initializing a reinforcement learning environment in which a retrieval system serves as an external feedback mechanism for evaluating prompt embedding transformations;

defining a state space comprising prompt embedding vectors prior to modification;

defining an action space comprising numerical transformations applied to the prompt embedding vectors within an embedding space;

defining a reward function that assigns positive rewards for decreasing proximity between modified prompt embeddings and non-relevant data set blocks while maintaining or increasing proximity to relevant blocks;

iteratively training the model by modifying prompt embeddings and retrieving blocks from the data set based on similarity to the modified embeddings;

computing a reward signal based on a retrieval quality of selected blocks relative to the prompt embedding vector; and repeating training over multiple query-block instances.

4. The computer-implemented method of claim 1, wherein the generated response is also based on the prompt.

5. The computer-implemented method of claim 1, wherein the generated response is also based on the modified prompt embedding vector.

6. The computer-implemented method of claim 1, wherein quantifying the amount of influence of the respective block comprises calculation of at least one of the following: a model loss associated with the respective data block to be removed from the selected data blocks, an attention weight from the respective data block, a log-odds score, or a likelihood ratio.

7. The computer-implemented method of claim 1, further comprising:

creating, with the computer system, a representation of modifications applied to the prompt embedding vector;

inputting, with the computer system, the representation of the modifications to a generative AI model; and generating, with the computer system, a natural language explanation describing the modifications made to the prompt embedding vector using the generative AI model.

8. The computer-implemented method of claim 1, further comprising regenerating the modified prompt embedding vector in response to determining that the response fails to meet a fidelity threshold.

9. The computer-implemented method of claim 1, wherein quantifying the influence of each selected block on the generated response comprises:

determining, with the computer system, a numerical representation of each selected block by mapping the text of the block to a multi-dimensional vector space;

determining, with the computer system, a numerical representation of the generated response by mapping the text of the response to the multi-dimensional vector space;

associating, with the computer system, individual portions of the generated response with corresponding portions of the selected blocks based on the proximity of their numerical representations within the vector space;

computing, with the computer system, a measure of contribution for each selected block by aggregating proximity values between its numerical representation and the numerical representations of the associated portions of the generated response; and normalizing, with the computer system, the measure of contribution across all selected blocks.

10. The computer-implemented method of claim 1, wherein the provided representation of the quantified amount of influence comprises:

associations between selected blocks and corresponding portions of the generated response; and a value for each of the corresponding to selected blocks, wherein each value represents a measure of contribution of the respective selected block to the corresponding portion of the response.

11. The computer-implemented method of claim 1, wherein modifying the prompt embedding vector comprises providing a reformulated query using a natural language processing model trained based on retrieval accuracy.

12. The computer-implemented method of claim 1, wherein the data set is indexed by computing embedding vectors in the embedding space of text blocks using hierarchical navigable small world graphs or content-aware chunking strategies.

13. The computer-implemented method of claim 1, wherein providing the representation of the quantified influence comprises providing data or instructions used to form a graphical user interface mapping response text segments to corresponding retrieved sources using a provenance-tracking visualization.

14. The computer-implemented method of claim 1, wherein modifying the prompt embedding vector comprises adjusting the vector representation based on stored session history data.

15. The computer-implemented method of claim 1, wherein selecting blocks comprises federated retrieval across corpora.

16. The computer-implemented method of claim 1, further comprising reranking the selected blocks based on proximity to the prompt embedding vector in the embedding space before generating the response.

17. The computer-implemented method of claim 1, wherein the method is implemented in a healthcare AI system, wherein retrieved blocks comprise medical records, clinical guidelines, research articles, or diagnostic data, and wherein the generated response includes at least one of: patient-specific recommendations based on retrieved clinical data, summaries of medical literature with ranked provenance scores, diagnostic support by correlating patient symptoms with retrieved cases, or drug interaction analysis based on pharmaceutical and clinical trial data.

18. The computer-implemented method of claim 1, wherein the quantifying for each of at least one of the selected blocks comprises steps for quantifying the blocks.

19. The computer-implemented method of claim 1, wherein the modifying the prompt embedding vector comprises steps for adjusting prompt embedding vectors to decrease proximity to vectors of blocks in a data set.

20. A tangible, non-transitory, machine-readable medium storing instructions that when executed by a data processing apparatus cause the data processing apparatus to perform operations comprising: the operations of any one of embodiments 1-19.

21. A system, comprising: one or more processors; and memory storing instructions that when executed by the processors cause the processors to effectuate operations comprising:

obtaining, with a computer system, a prompt that is, or is part of, a request for a generative artificial intelligence (AI) model to generate a response;

determining, with the computer system, a prompt embedding vector representing the prompt in an embedding space, wherein proximity within the embedding space at least partially corresponds to semantic similarity;

modifying, with the computer system, the prompt embedding vector using a trained model configured to adjust prompt embedding vectors to decrease proximity to vectors of blocks in a data set from which data is retrieved to augment generation by the generative AI model;

determining, with the computer system, that the modified prompt embedding vector is within a threshold distance to vectors in the embedding space corresponding to one or more blocks in the data set and, in response, selecting the one or more blocks in the data set;

generating, with the computer system, a response using the generative AI model based on the selected one or more blocks in the data set;

quantifying, with the computer system, for each of at least one of the selected blocks, an amount of influence of the respective block on corresponding text in the generated response; and providing, with the computer system, the response and a representation of the quantified amount of influence as an output.

What is claimed is:

1. A computer-implemented method, comprising:

obtaining, with a computer system, a prompt that is, or is part of, a request for a generative artificial intelligence (AI) model to generate a response;

determining, with the computer system, a prompt embedding vector representing the prompt in an embedding space, wherein proximity within the embedding space at least partially corresponds to semantic similarity;

modifying, with the computer system, the prompt embedding vector using a trained model configured to adjust prompt embedding vectors to decrease proximity to vectors of blocks of data in a data set from which data is retrieved to augment generation by the generative AI model, wherein the trained model configured to adjust prompt embedding vectors is trained by:

initializing a reinforcement learning environment in which a retrieval system serves as external feedback for evaluating prompt embedding vector transformations;

defining a state space comprising training prompt embedding vectors prior to modification;

defining an action space comprising numerical transformations applied to the training prompt embedding vectors within the embedding space;

defining a reward function that assigns rewards for decreasing proximity between modified training prompt embedding vectors and non-relevant blocks of data while maintaining or increasing proximity to relevant blocks;

iteratively training the model by modifying training prompt embedding vectors and retrieving blocks from a training data set based on similarity to the modified training prompt embedding vectors;

computing a reward signal based on a retrieval quality of selected training blocks relative to the training prompt embedding vectors; and repeating training steps over multiple prompt-block instances;

determining, with the computer system, that the modified prompt embedding vector is within a threshold distance to one or more vectors in the embedding space corresponding to one or more blocks of data in the data set and, in response, selecting the one or more blocks of data in the data set;

generating, with the computer system, a response using the generative AI model based on the selected one or more blocks of data in the data set;

quantifying, with the computer system, for each of at least one of the selected blocks, an amount of influence of the respective block on corresponding text in the generated response; and providing, with the computer system, the response and a representation of the quantified amount of influence as an output.

2. The method of claim 1, wherein:

the data set comprises a corpus of more than 10,000 natural language text documents;

modifying comprises changing scalars of the prompt embedding vector;

selecting the one or more blocks comprises selecting chunks of the natural language text documents; and the embedding space has more than 256 dimensions.

3. The computer-implemented method of claim 1, wherein the generated response is also based on the prompt.

4. The computer-implemented method of claim 1, wherein the generated response is also based on the modified prompt embedding vector.

5. The computer-implemented method of claim 1, wherein quantifying the amount of influence of the respective block comprises calculation of at least one of the following: a model loss associated with the respective block to be removed from the selected blocks of data, an attention weight from the respective data block, a log-odds score, or a likelihood ratio.

6. The computer-implemented method of claim 1, further comprising:

creating, with the computer system, a representation of modifications applied to the prompt embedding vector;

inputting, with the computer system, the representation of the modifications to the generative AI model; and generating, with the computer system, a natural language explanation describing the modifications made to the prompt embedding vector using the generative AI model.

7. The computer-implemented method of claim 1, further comprising regenerating the modified prompt embedding vector in response to determining that the response fails to meet a fidelity threshold.

8. The computer-implemented method of claim 1, wherein quantifying the influence of each selected block on the generated response comprises:

determining, with the computer system, a numerical representation of each selected block by mapping the text of the block to a multi-dimensional vector space;

determining, with the computer system, a numerical representation of the generated response by mapping the text of the response to the multi-dimensional vector space;

associating, with the computer system, individual portions of the generated response with corresponding portions of the selected blocks based on the proximity of their numerical representations within the vector space;

computing, with the computer system, a measure of contribution for each selected block by aggregating proximity values between its numerical representation and the numerical representations of the associated portions of the generated response; and normalizing, with the computer system, the measure of contribution across all selected blocks.

9. The computer-implemented method of claim 1, wherein the provided representation of the quantified amount of influence comprises:

associations between selected blocks and corresponding portions of the generated response; and a value corresponding to each of the selected blocks, wherein each value corresponding to selected blocks represents a measure of contribution of the respective selected block to the corresponding portion of the response.

10. The computer-implemented method of claim 1, wherein modifying the prompt embedding vector comprises providing a reformulated query using a natural language processing model trained based on retrieval accuracy.

11. The computer-implemented method of claim 1, wherein the data set is indexed by computing embedding vectors in the embedding space of text blocks using a hierarchical navigable small world graph.

12. The computer-implemented method of claim 1, wherein providing the representation of the quantified influence comprises providing data or instructions used to form a graphical user interface mapping response text segments to corresponding retrieved sources using a provenance-tracking visualization.

13. The computer-implemented method of claim 1, wherein modifying the prompt embedding vector comprises adjusting the vector representation based on stored session history data.

14. The computer-implemented method of claim 1, wherein selecting blocks comprises federated retrieval across corpora.

15. The computer-implemented method of claim 1, further comprising reranking the selected blocks based on proximity to the prompt embedding vector in the embedding space before generating the response.

16. The computer-implemented method of claim 1, wherein the method is implemented in a healthcare AI system, wherein retrieved blocks comprise medical records, clinical guidelines, research articles, or diagnostic data, and wherein the generated response includes at least one of: patient-specific recommendations based on retrieved clinical data, summaries of medical literature with ranked provenance scores, diagnostic support by correlating patient symptoms with retrieved cases, or drug interaction analysis based on pharmaceutical and clinical trial data.

17. The computer-implemented method of claim 1, wherein the quantifying for each of at least one of the selected blocks comprises steps for quantifying the blocks.

18. The computer-implemented method of claim 1, wherein the modifying the prompt embedding vector comprises steps for adjusting prompt embedding vectors to decrease proximity to vectors of blocks in a data set.

19. A computer-implemented method, comprising:

obtaining, with a computer system, a prompt that is, or is part of, a request for a generative artificial intelligence (AI) model to generate a response;

determining, with the computer system, a prompt embedding vector representing the prompt in an embedding space, wherein proximity within the embedding space at least partially corresponds to semantic similarity;

modifying, with the computer system, the prompt embedding vector using a trained model configured to adjust prompt embedding vectors to decrease proximity to vectors of blocks of data in a data set from which data is retrieved to augment generation by the generative AI model;

determining, with the computer system, that the modified prompt embedding vector is within a threshold distance to one or more vectors in the embedding space corresponding to one or more blocks of data in the data set and, in response, selecting the one or more blocks of data in the data set;

generating, with the computer system, a response using the generative AI model based on the selected one or more blocks of data in the data set;

quantifying, with the computer system, for each of at least one of the selected blocks, an amount of influence of the respective block on corresponding text in the generated response;

providing, with the computer system, the response and a representation of the quantified amount of influence as an output;

creating, with the computer system, a representation of modifications applied to the prompt embedding vector;

inputting, with the computer system, the representation of the modifications to the generative AI model; and generating, with the computer system, a natural language explanation describing the modifications made to the prompt embedding vector using the generative AI model.

20. The computer-implemented method of claim 19, wherein the generated response is also based on the prompt.

21. The computer-implemented method of claim 19, wherein the generated response is also based on the modified prompt embedding vector.

22. The computer-implemented method of claim 19, wherein quantifying the amount of influence of the respective block comprises calculation of at least one of the following: a model loss associated with the respective block to be removed from the selected data blocks, an attention weight from the respective block of data, a log-odds score, or a likelihood ratio.

23. The computer-implemented method of claim 19, further comprising regenerating the modified prompt embedding vector in response to determining that the response fails to meet a fidelity threshold.

24. The computer-implemented method of claim 19, wherein providing the representation of the quantified influence comprises providing data or instructions used to form a graphical user interface mapping response text segments to corresponding retrieved sources using a provenance-tracking visualization.

25. The computer-implemented method of claim 19, wherein the method is implemented in a healthcare AI system, wherein retrieved blocks comprise medical records, clinical guidelines, research articles, or diagnostic data, and wherein the generated response includes at least one of: patient-specific recommendations based on retrieved clinical data, summaries of medical literature with ranked provenance scores, diagnostic support by correlating patient symptoms with retrieved cases, or drug interaction analysis based on pharmaceutical and clinical trial data.

26. A computer-implemented method, comprising:

obtaining, with a computer system, a prompt that is, or is part of, a request for a generative artificial intelligence (AI) model to generate a response;

determining, with the computer system, a prompt embedding vector representing the prompt in an embedding space, wherein proximity within the embedding space at least partially corresponds to semantic similarity;

modifying, with the computer system, the prompt embedding vector using a trained model configured to adjust prompt embedding vectors to decrease proximity to vectors of blocks of data in a data set from which data is retrieved to augment generation by the generative AI model;

determining, with the computer system, that the modified prompt embedding vector is within a threshold distance to vectors in the embedding space corresponding to one or more blocks of data in the data set and, in response, selecting the one or more blocks of data in the data set;

generating, with the computer system, a response using the generative AI model based on the selected one or more blocks of data in the data set;

quantifying, with the computer system, for each of at least one of the selected blocks, an amount of influence of the respective block on corresponding text in the generated response, the quantifying comprising:

determining, with the computer system, a numerical representation of each selected block by mapping the text of the block to a multi-dimensional vector space;

determining, with the computer system, a numerical representation of the generated response by mapping the text of the response to the multi-dimensional vector space;

associating, with the computer system, individual portions of the generated response with corresponding portions of the selected blocks based on the proximity of their numerical representations within the vector space;

computing, with the computer system, a measure of contribution for each selected block by aggregating proximity values between its numerical representation and the numerical representations of the associated portions of the generated response; and normalizing, with the computer system, the measure of contribution across all selected blocks; and providing, with the computer system, the response and a representation of the quantified amount of influence as an output.

27. The computer-implemented method of claim 26, wherein the provided representation of the quantified amount of influence comprises:

associations between selected blocks and corresponding portions of the generated response; and a value corresponding to each of the selected blocks, wherein each value corresponding to selected blocks represents a measure of contribution of the respective selected block to the corresponding portion of the response; and wherein the multi-dimensional vector space is the embedding space.

28. The method of claim 26, wherein:

the data set comprises a corpus of more than 10,000 natural language text documents;

modifying comprises changing scalars of the prompt embedding vector;

selecting the one or more blocks comprises selecting chunks of the natural language text documents; and the embedding space has more than 256 dimensions.

29. The computer-implemented method of claim 26, wherein quantifying the amount of influence of the respective block comprises calculation of at least one of the following: a model loss associated with the respective block to be removed from the selected data blocks, an attention weight from the respective block of data, a log-odds score, or a likelihood ratio.

30. The computer-implemented method of claim 26, further comprising reranking the selected blocks based on proximity to the prompt embedding vector in the embedding space before generating the response.

31. The computer-implemented method of claim 26, wherein the quantifying for each of at least one of the selected blocks comprises steps for quantifying the blocks.

32. The computer-implemented method of claim 26, wherein providing the representation of the quantified influence comprises providing data or instructions used to form a graphical user interface mapping response text segments to corresponding retrieved sources using a provenance-tracking visualization.

33. A computer-implemented method, comprising:

obtaining, with a computer system, a prompt that is, or is part of, a request for a generative artificial intelligence (AI) model to generate a response;

determining, with the computer system, a prompt embedding vector representing the prompt in an embedding space, wherein proximity within the embedding space at least partially corresponds to semantic similarity;

modifying, with the computer system, the prompt embedding vector using a trained model configured to adjust prompt embedding vectors to decrease proximity to vectors of blocks of data in a data set from which data is retrieved to augment generation by the generative AI model;

determining, with the computer system, that the modified prompt embedding vector is within a threshold distance to vectors in the embedding space corresponding to one or more blocks of data in the data set and, in response, selecting the one or more blocks of data in the data set;

generating, with the computer system, a response using the generative AI model based on the selected one or more blocks of data in the data set;

quantifying, with the computer system, for each of at least one of the selected blocks, an amount of influence of the respective block on corresponding text in the generated response; and providing, with the computer system, the response and a representation of the quantified amount of influence as an output, wherein the provided representation of the quantified amount of influence comprises:

associations between selected blocks and corresponding portions of the generated response; and a value corresponding to each of the selected blocks, wherein each value corresponding to selected blocks represents a measure of contribution of the respective selected block to the corresponding portion of the response.

34. The computer-implemented method of claim 33, wherein the generated response is also based on the prompt.

35. The computer-implemented method of claim 33, wherein the generated response is also based on the modified prompt embedding vector.

36. The computer-implemented method of claim 33, wherein quantifying the amount of influence of the respective block comprises calculation of at least one of the following: a model loss associated with the respective block to be removed from the selected blocks of data, an attention weight from the respective data block, a log-odds score, or a likelihood ratio.

37. The computer-implemented method of claim 33, further comprising regenerating the modified prompt embedding vector in response to determining that the response fails to meet a fidelity threshold.

38. The computer-implemented method of claim 33, wherein providing the representation of the quantified influence comprises providing data or instructions used to form a graphical user interface mapping response text segments to corresponding retrieved sources using a provenance-tracking visualization.

39. The computer-implemented method of claim 33, wherein the method is implemented in a healthcare AI system, wherein retrieved blocks comprise medical records, clinical guidelines, research articles, or diagnostic data, and wherein the generated response includes at least one of: patient-specific recommendations based on retrieved clinical data, summaries of medical literature with ranked provenance scores, diagnostic support by correlating patient symptoms with retrieved cases, or drug interaction analysis based on pharmaceutical and clinical trial data.

40. The computer-implemented method of claim 33, wherein:

the data set comprises a corpus of more than 10,000 natural language text documents;

modifying comprises changing scalars of the prompt embedding vector;

selecting the one or more blocks comprises selecting chunks of the natural language text documents; and the embedding space has more than 256 dimensions.

* * * * *